(12) United States Patent　　　(10) Patent No.:　US 12,605,265 B2
Johns　　　　　　　　　　　　　(45) Date of Patent:　　Apr. 21, 2026

(54) ORTHOPEDIC BACK SUPPORT CORSET

(71) Applicant: Kathrine A. Johns, Bigfork, MT (US)

(72) Inventor: Kathrine A. Johns, Bigfork, MT (US)

( * ) Notice: Subject to any disclaimer, the term of this patent is extended or adjusted under 35 U.S.C. 154(b) by 206 days.

(21) Appl. No.: 18/442,018

(22) Filed: Feb. 14, 2024

(65) Prior Publication Data

US 2025/0255743 A1　　Aug. 14, 2025

(51) Int. Cl.
*A61F 5/02* (2006.01)

(52) U.S. Cl.
CPC .................................... *A61F 5/028* (2013.01)

(58) Field of Classification Search
CPC .... A61F 5/028; A61F 5/01; A61F 5/00; A61F 2007/0024; A61F 2007/0025; A61F 2007/0026; A61F 2007/0027
See application file for complete search history.

(56) References Cited

U.S. PATENT DOCUMENTS

| | | | | |
|---|---|---|---|---|
| 1,923,112 | A | * | 8/1933 | Nickerson ................ A41C 1/08 |
| | | | | D2/702 |
| 3,149,634 | A | * | 9/1964 | Martin ..................... A41C 1/06 |
| | | | | 450/132 |
| 3,931,816 | A | | 1/1976 | Waldmann |
| 4,120,297 | A | | 10/1978 | Rabischong |
| 4,541,419 | A | | 9/1985 | Osawa |
| 4,681,113 | A | | 7/1987 | Coplans |
| 4,926,502 | A | | 5/1990 | Miyamura |
| 5,634,891 | A | | 6/1997 | Beczak, Sr. |
| 5,908,346 | A | | 6/1999 | McCall |
| 6,755,799 | B2 | | 6/2004 | Toda |
| 8,695,115 | B2 | * | 4/2014 | Leyva ...................... A41D 1/00 |
| | | | | 450/97 |
| 8,795,215 | B2 | | 8/2014 | Rossi |
| 10,322,309 | B2 | | 6/2019 | Feldman |
| 10,433,592 | B2 | * | 10/2019 | Olshansky ............. A41C 1/003 |
| 10,667,569 | B2 | | 6/2020 | Fay |
| 2007/0077859 | A1 | | 4/2007 | Walker |
| 2013/0326788 | A1 | | 12/2013 | Bell |
| 2019/0231011 | A1 | | 8/2019 | Patton |
| 2020/0237547 | A1 | * | 7/2020 | Joseph ................... A61F 5/028 |
| 2021/0007872 | A1 | | 1/2021 | Shipley |
| 2021/0259873 | A1 | | 8/2021 | Lyzhyn |
| 2022/0132940 | A1 | | 5/2022 | Beard |

FOREIGN PATENT DOCUMENTS

| | | |
|---|---|---|
| EP | 0152035 A2 | 8/1985 |
| EP | 0649608 A1 | 4/1995 |
| GB | 1432945 A | 4/1976 |

(Continued)

*Primary Examiner* — Tarla R Patel

(74) *Attorney, Agent, or Firm* — Lowenstein Sandler LLP

(57) ABSTRACT

Orthopedic corsets with bonings in a back-support panel are described. One orthopedic corset includes a first panel, a second panel, and a fastener to fasten the first panel and the second panel at a front side of the orthopedic corset. The orthopedic corset also includes a third panel, a fourth panel, a lacing system, and a back-support panel. The lacing system is located at the back side of the orthopedic corset and adjusts a tightness of the orthopedic corset. The back-support panel is coupled between the third panel and the fourth panel, and is located behind the lacing system. The back-support panel includes one or more bonings.

20 Claims, 20 Drawing Sheets

(56) References Cited

FOREIGN PATENT DOCUMENTS

| GB | 2435606 | A | 9/2007 |
|----|---------|----|---------|
| GB | 2484949 | A | 5/2012 |
| WO | 9406375 | A1 | 3/1994 |
| WO | 9961103 | A1 | 12/1999 |
| WO | 02100304 | A1 | 12/2002 |
| WO | 2004043307 | A1 | 5/2004 |
| WO | 2010042080 | A1 | 4/2010 |
| WO | 2012098424 | A1 | 7/2012 |
| WO | 2015139076 | A1 | 9/2015 |
| WO | 2016105213 | A1 | 6/2016 |

* cited by examiner

ORTHOPEDIC CORSET
(FRONT VIEW)

ORTHOPEDIC CORSET
(RIGHT SIDE VIEW)

250

STRETCH
FABRIC
252 casing interior
view: bonded
interfacing to
act as barrier
to prevent
fabric puncture
from boning

334

306

336 outer
casing

300

306

302

300

304

BACK SECTION
(CROSS-SECTIONAL
VIEW)
220

RIGHT SIDE SECTION
(CROSS-SECTIONAL VIEW)
246

LEFT SIDE SECTION
(CROSS-SECTIONAL VIEW)
248

BACK SECTION
(CROSS-SECTIONAL
BOTTOM VIEW)
220

FRONT SECTION
(CROSS-SECTIONAL VIEW)
<u>402</u>

FRONT SECTION
(FRONT VIEW)

FRONT SECTION
(REAR VIEW) 402

BACK SECTION

FRONT
SECTION

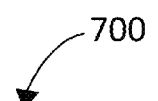

700

---

SEW TAPE OF A ZIPPER INTO A RIGHT EDGE OF A FIRST RIGHT PANEL AND A RIGHT EDGE OF A FIRST LEFT PANEL TO PERMIT THE ZIPPER TO FASTEN THE FIRST RIGHT PANEL AND THE FIRST LEFT PANEL AT A FRONT SIDE OF THE ORTHOPEDIC CORSET 702

↓

DISPOSE A FIRST THERMOPLASTIC MATERIAL ON A FIRST END OF AN ELONGATED BONING 704

↓

DISPOSE A SECOND THERMOPLASTIC MATERIAL ON A SECOND END OF THE ELONGATED BONING 706

↓

SEW A CASING COMPRISING THE ELONGATED BONING 708

↓

SEW THE CASING IN A BACK-SUPPORT PANEL 710

↓

SEW A RIGHT EDGE OF THE BACK-SUPPORT PANEL, A RIGHT EDGE OF A FIRST LACING PANEL, AND A RIGHT EDGE OF A SECOND RIGHT PANEL AT A FIRST SEAM AT A BACK SIDE OF THE ORTHOPEDIC CORSET 712

↓

SEW A LEFT EDGE OF THE BACK-SUPPORT PANEL, A RIGHT EDGE OF A SECOND LACING PANEL, AND A RIGHT EDGE OF A SECOND LEFT PANEL AT A SECOND SEAM AT THE BACK SIDE OF THE ORTHOPEDIC CORSET 714

FIG. 7

ORTHOPEDIC BACK SUPPORT CORSET

BACKGROUND

A corset is a garment meticulously crafted to snugly encase the torso, sculpting it into an aesthetically pleasing shape, often accentuating a cinched waist and enhanced hips and bust. This form-fitting piece is distinguished by its structured architecture, fortified with boning, and tightened with lacing, enabling it to dramatically transform the wearer's silhouette. Historically, corsets were central to fashion, serving primarily to mold the body into the prevailing idealized contours of each era. These garments have traversed an evolutionary journey through fashion history, continuously adapting in style to mirror the shifting trends and societal values of different periods.

In contemporary times, the corset's role extends beyond mere fashion; it is embraced for historical reenactments, body modification, theatrical costuming, and as a statement piece in modern wardrobes. The enduring allure of corsets is a testament to their versatility and the shifting perceptions of beauty and femininity. Their design and popularity have oscillated, mirroring the ever-evolving landscape of fashion and societal attitudes towards the female form.

BRIEF DESCRIPTION OF THE DRAWINGS

The present disclosure is illustrated by way of example, and not by way of limitation, in the figures of the accompanying drawings.

FIG. 7 illustrates a method of manufacturing an orthopedic corset according to at least one embodiment.

DETAILED DESCRIPTION

Figures 1A, 1B:
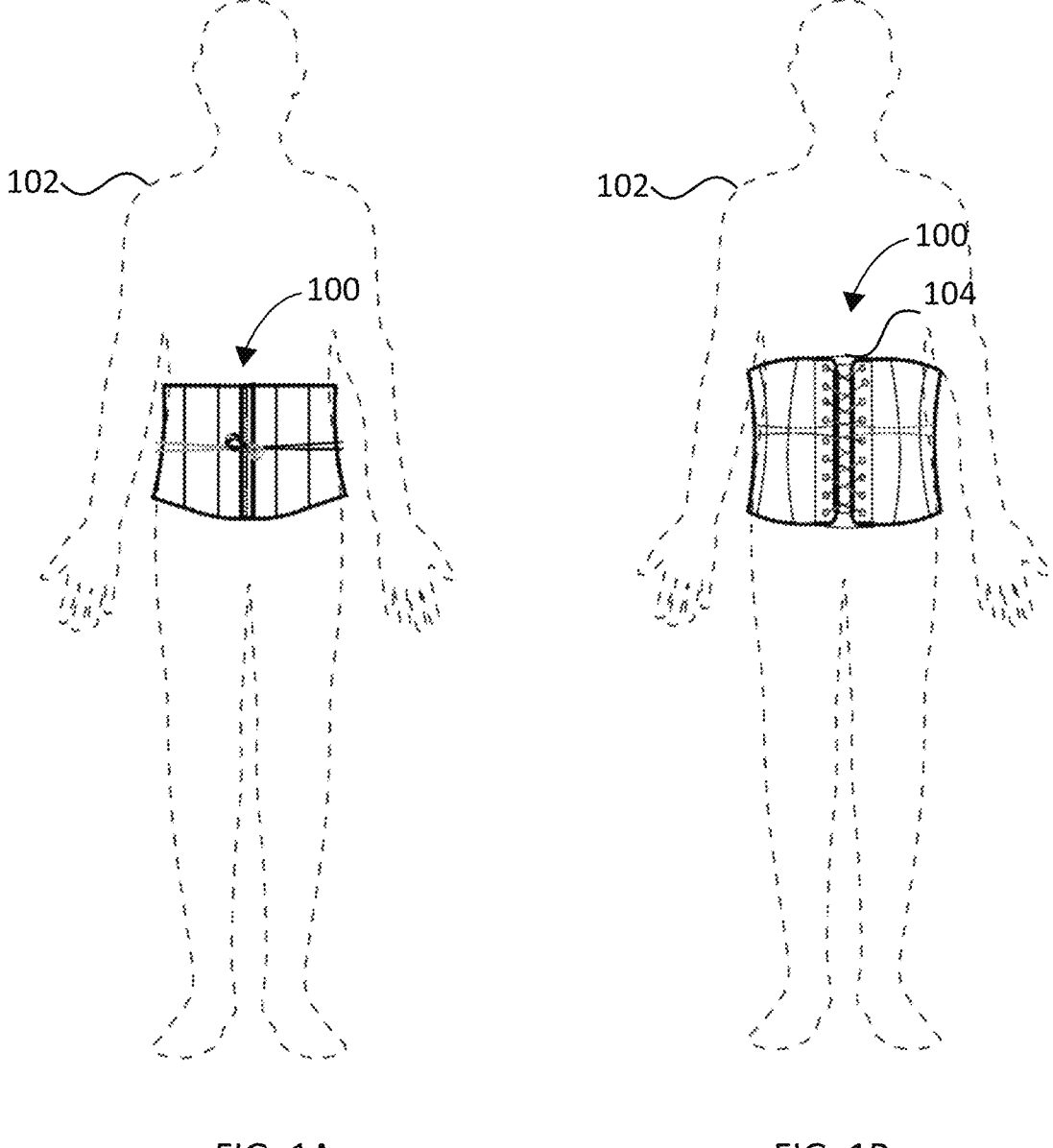
FIG. 1A is a front view of an orthopedic corset worn by a person according to at least one embodiment.
FIG. 1B is a back view of the orthopedic corset of FIG. 1A worn by the person according to at least one embodiment.

Orthopedic corsets with bonings in a back-support panel are described. Originally crafted to sculpt a fashionable silhouette, corsets have found utility beyond mere aesthetics, venturing into the realm of generic spine and torso support. Notably, they facilitate an upright posture; the interplay of rigid boning and snug lacing combats the tendency to slouch, thereby encouraging a straighter spine and a more dignified posture. Constructed from durable yet pliable materials such as cotton, satin, or leather, corsets are reinforced with boning—historically, made from whalebone but now commonly crafted from steel or plastic. This boning is the cornerstone of the corset's structure and its ability to shape the body. Corsets are engineered as a single, cohesive garment, assembled from multiple fabric panels meticulously stitched together. They envelop the wearer's torso, extending from the bust to the hips, and are secured with lacing at the back for customizable tightness. Many designs incorporate a busk, a front closure featuring two steel pieces that interlock, adding support and simplifying the process of donning and doffing the corset.

While corsets contribute to a more erect posture, it is important to note that they are not specifically tailored for orthopedic back support. Their primary design focus remains on body contouring and fashion, with health-related benefits being secondary considerations.

A corset is intricately composed of several fundamental components, such as panels, boning, a busk, lacing, eyelets or grommets, waist tape, binding, and, optionally, a modesty panel. While modern corsets might deviate in construction and materials, these elements remain hallmarks of traditional corsetry.

At the heart of the corset are the panels, individual fabric pieces meticulously sewn together to sculpt the corset's form. Providing its core structure and contouring ability is the boning, historically crafted from whalebone but now predominantly fashioned from steel or plastic in contemporary designs. The busk, a pivotal hardware element positioned at the corset's front, comprises two elongated steel pieces-one adorned with loops and the other with corresponding posts. This duo interlocks to securely fasten the corset's front.

The back of the corset features lacing-typically a robust cord or ribbon-threaded through strategically placed eyelets or grommets. This design not only reinforces the lacing holes but also allows for precise fit adjustments. Ensuring even tension distribution and maintaining the corset's silhouette, the waist tape is a sturdy fabric strip sewn internally around the waist. To refine and protect, the binding, often made from bias tape, elegantly covers the panel edges.

An optional yet functional element is the modesty panel, nestled beneath the lacing at the back. It serves dual purposes: protecting the skin from direct contact with the lacing and concealing any exposed skin.

It is crucial to note, however, that despite the corset's capability to offer general back support, its structure-particularly the lacing system and the optional modesty panel—is not engineered to provide orthopedic back support. The assemblage of these components achieves the corset's iconic shape and support but does not cater to specialized orthopedic needs.

An orthopedic back strap, also referred to as a back brace or lumbar support brace, serves as a vital medical device designed to reinforce the back, with a specific emphasis on the lumbar region. This brace is integral in managing back pain, enhancing stability, and correcting posture in individuals suffering from various back ailments, including herniated discs, sciatica, scoliosis, and general lower back pain. The brace's support is key to alleviating discomfort and aiding in the recovery process post-injury or surgery. It also plays a preventive role in activities that pose a risk to the back, such as heavy lifting or strenuous physical labor.

Constructed from a spectrum of materials ranging from flexible to rigid, these braces often incorporate adjustable straps and Velcro closures to ensure a personalized and secure fit. Advanced designs might also feature lumbar pads, shoulder straps, or reinforcements made of metal or plastic for augmented support. This diversity in design enables the availability of various braces, from straightforward elastic belts to more sophisticated structures that cater to specific medical requirements.

Despite their functional importance, orthopedic back straps often face challenges regarding aesthetics. Generally, these braces lack attention to fashion, being made from non-garment materials and typically presented in stark, generic colors like black or white. This design approach leads to a distinctly medical appearance, which may not be visually appealing or discreet under clothing. The practical yet conspicuous appearance of these straps, marked by their Velcro closures and belt-like structure, provides little in terms of style or concealment, potentially drawing unwanted attention to the wearer. This lack of cosmetic consideration can be a drawback for individuals who are conscious about the visual impact of wearing such a medical device in public or social settings.

Aspects and embodiments of the present disclosure overcome the deficiencies described above and others by providing an orthopedic corset (also referred to as an "orthopedic back support corset") with structural features to provide orthopedic back support to a person wearing it. One orthopedic corset includes a first panel, a second panel, and a fastener to fasten the first panel and the second panel at a front side of the orthopedic corset. The orthopedic corset also includes a third panel, a fourth panel, a lacing system, and a back-support panel. The lacing system is located at the back side of the orthopedic corset and adjusts a tightness of the orthopedic corset. The back-support panel is coupled between the third panel and the fourth panel, and is located behind the lacing system. The back-support panel includes one or more bonings (also referred to herein as boning members). The boning can be a steel boning that flexes in only two directions. The boning can be a spiral steel boning that flexes in two or more directions. The boning can be a plastic boning.

The boning can be used to provide structure and shape to the orthopedic corset, as well as provide orthopedic support to the spine and torso of the wearer. In particular, the boning members of the back-support panel, and their relative placement at the back of the orthopedic corset provide the orthopedic support to the wearer in a similar manner as orthopedic back straps, but as an aesthetically appealing garment. The boning members can be made of rigid or semirigid materials, such as steel, plastic, metal, animal bone material, or the like. In at least one embodiment, the boning is an elongated boning of metal or plastic that is sewn in a casing that is secured to outer fabric of a panel, such as the back-support panel 104. A casing in sewing is a tunnel or enclosed space created in the fabric, often used for inserting elastic, drawstrings, or other elements. In this case, the boning member can be inserted into the casing. In some cases, interface fabric can be bonded to a casing. This refers to the process of attaching interfacing to a specific part of a garment or fabric item to provide additional structure and support. In some cases, the back-support panel 104 can have material that is more flexible than the material of the two adjoining panels, so the elongated boning is sewn into a casing that is secured (e.g., sewn) to the flexible material of the back-support panel 104. In other cases, the boning can be sewn into casings that are secured to the outer fabric of the panel. The outer fabric can also be referred to as shell fabric or facing for the exterior fabric.

In other cases, the boning can be disposed between the outer fabric and a liner of a panel. In some embodiments, a first thermoplastic material is disposed on a first end of the elongated boning, and a second thermoplastic material is disposed on a second end of the elongated boning. The thermoplastic material can be used to prevent rough or sharp edges of the elongated boning from snagging or tearing the fabric of the casing and/or panel. In other embodiments, other types of bonded interfacing materials or coatings can be applied to the elongated boning before being disposed in fabric of the orthopedic corset 100. The bonings are described in more detail below with respect to FIG. 3A to FIG. 4A. The bonings of the back-support panel 104 provide orthopedic support to the spine and torso of the wearer.

Another orthopedic corset includes a back-support panel located at the back of the orthopedic corset. The back-support panel spans across a gap between two segments (e.g., panels) of the orthopedic corset that accommodate the lacing. At the back of the orthopedic corset, the lacing, which is usually a strong cord or ribbon, is threaded through eyelets or grommets on these two segments. The lacing, when strung through the eyelets or grommets, allows the orthopedic corset to be tightened and adjusted for fit. The eyelets or grommets are metal or plastic rings that are inserted into holes in these two segments of fabric at the back of the orthopedic corset. The lacing allows the two segments of the orthopedic corset to be closed together and tightened or loosened to adjust for fit. The back-support panel is located behind the lacing and two segments. That is, the back-support panel is located closer to the wearer's back than the two segments and lacing. The back-support panel includes one or more bonings as described herein.

FIG. 1A is a front view of an orthopedic corset 100 worn by a person 102 according to at least one embodiment. FIG. 1B is a back view of the orthopedic corset 100 of FIG. 1A worn by the person 102 according to at least one embodiment. The orthopedic corset 100 has a back section with multiple panels, a front section with multiple panels, and two side sections with panels. The back section of the orthopedic corset 100 includes at least the back-support panel 104 located behind a lacing system. The lacing system can be coupled to adjacent panels of the back section. In general, such as illustrated in FIG. 1A and FIG. 1B, the back section has two segments, such as two separate panels, adjusted by the lacing system, and the front section has two segments, such as two separate panels that are joined using a fastener. The fastener is a mechanical device that is used to join two edges of fabric of these two segments together. In at least one embodiment, the fastener is a zipper. In some embodiments, the fastener is a busk or a busk closure. The busk is a piece of hardware at the front of the corset. It includes two long pieces of metal (e.g., steel), one with loops and the other with posts, which fasten together to close the front of the orthopedic corset. The busk can also provide additional support and can add to the ease of putting on and taking off the garment. Alternatively, other fasteners can be used to join the two segments at the front section of the orthopedic corset 100.

The lacing system can include reinforcement rings, such as eyelets, grommets, or lace hooks, and lacing (one or two laces). As illustrated in FIG. 1A and FIG. 1B, the lacing can be long enough to be threaded through eyelets or grommets in the back section, and be reachable by a wearer to bring the lacing to the front section. The wearer can pull the lacing at the front section to the desired tightness and tie the lacing in a bow or other knot against the front section of the orthopedic corset 100, as illustrated in FIG. 1A. In other embodiments, instead of a lacing system, the two segments of the back section can be joined using a fastener, such as a zipper. Although the fastener can be used for ease of putting on and taking off the orthopedic corset 100, a fastener at the back section can be hard for a wearer to fasten by themselves. Furthermore, depending on the type of fastener used at the back section, the capability to adjust the tightness of the orthopedic corset may be lost or reduced, as compared to a lacing system. Alternatively, other fasteners can be used to join the two segments at the back section of the orthopedic corset.

As described in more detail below, the back-support panel 104 can include multiple bonings. The bonings can be animal bone material, metal, plastic, or the like. For example, the back section can have the back-support panel 104 underneath a first lacing panel and a second lacing panel, each of which is coupled to adjacent panels in the back section, as illustrated in FIG. 1B. The back-support panel 104 can have a straight panel with bonings to provide support at a central area of the backside of the orthopedic corset 100, whereas the adjacent panels can have curved shapes with or without boning members to contour the shape of the orthopedic corset 100 in areas of the corset that are closer to the hips than the spine of the wearer.

The number of panels used in the orthopedic corset 100 can vary. For example, the orthopedic corset 100 can have eleven different panels and the two lacing panels. The back section can include five panels, including the back-support panel 104, and the front section can include four panels. The two side sections can each include a flexible panel that joins the back section and the front section. In other embodiments, the side sections can be panels like the panels of the front and back sections described above. The side sections may also have bonings to provide additional support on the sides of the wearer's torso. The orthopedic corset 100 can have more or less panels than eleven. In addition to the bonings in the back-support panel 104, the orthopedic corset 100 can have additional bonings in other panels of the orthopedic corset 100. The different panels of the orthopedic corset 100 are described in more detail below with respect to FIG. 2A to FIG. 2E.

FIG. 2A-FIG. 2D illustrate different views of an orthopedic corset 200 according to at least one embodiment. The orthopedic corset 200 can be similar to the orthopedic corset 100 as described above, except as otherwise noted in the description.

Figure 2A:
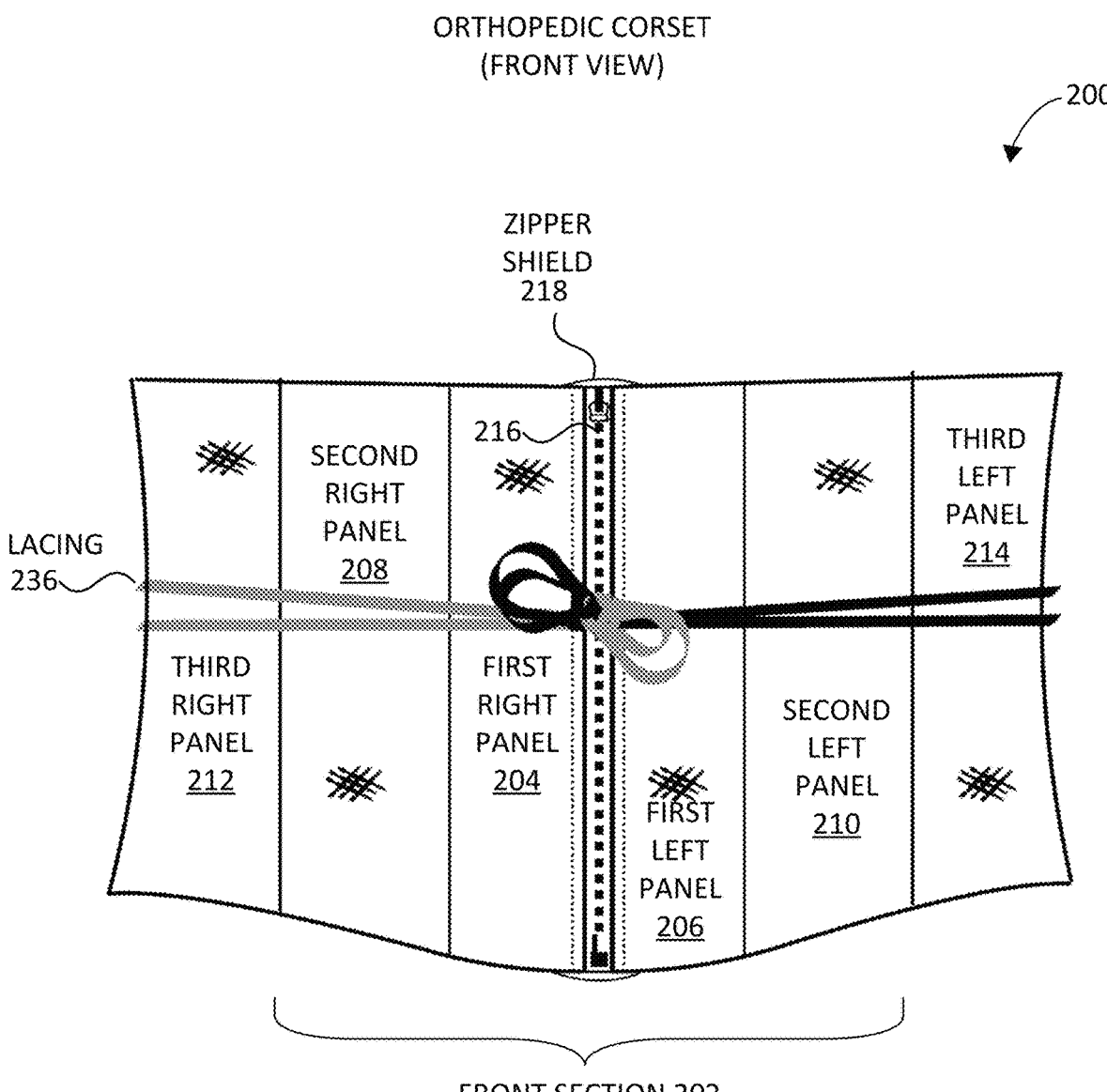
FIG. 2A illustrates a front section of an orthopedic corset according to at least one embodiment.

FIG. 2A illustrates a front section 202 of an orthopedic corset 200 according to at least one embodiment. The front section 202 includes a first right panel 204, a first left panel 206, a second right panel 208, a second left panel 210, a zipper 216, and a zipper shield 218. The first right panel 204 and the second right panel 208 are coupled together, for example, by sewing edges of the panels together at a seam. Similarly, the first left panel 206 and the second left panel 210 are coupled together, for example, by sewing edges of the panels together at a seam. A tape of the zipper 216 can be sewn into a right edge of the first right panel 204 and a right edge of the first left panel 206 to permit the zipper 216 to fasten the first right panel 204 and the first left panel 206 at a front side of the orthopedic corset 200. The first right panel 204 and first left panel 206 can be joined by closing the zipper 216. Alternatively, other fasteners can be used to join first right panel 204 and first left panel 206 at the front section 202. For example, the orthopedic corset 200 can include a busk or a busk closure on the front section 202. The zipper shield 218 (also referred to as "fly shield" or "zipper flap") can be coupled to one of the first right panel 204 or the first left panel 206. For example, the zipper shield 218 can be sewn at a left edge of the first right panel 204 or a left edge of the first left panel 206. Alternatively, the zipper shield 218 can be sewn at other locations of the front section 202. The zipper shield 218 is located behind the zipper 216 when the zipper 216 is closed. The zipper shield 218 can be used to prevent direct contact between skin or undergarments and the zipper 216. The zipper shield 218 lies under the zipper 216 to protect the skin or undergarment from getting stuck or pinched in the zipper 216 when fastening or unfastening the zipper 216 since the zipper 216 rests tight against the front abdomen. It is also possible to cover the outside surface of the orthopedic corset 200, such as to hide the zipper 216 from view when closed.

The front section 202 is coupled to two side sections, each having one panel. In particular, the second right panel 208 is coupled to a third right panel 212 on a right-side section 246 of the orthopedic corset 200 (see FIG. 2C), and the second left panel 210 is coupled to a third left panel 214 of a left-side section 248 (see FIG. 2D). The third right panel 212 and third left panel 214 can be flexible panels. In at least one embodiment, the panels of the front section 202 (e.g., first right panel 204, first left panel 206, second right panel 208, and second left panel 210) include outer fabric of a first material. The panels of the right-side section (i.e., third right panel 212) and the left-side section (i.e., third left panel 214) each include a fabric of a second material that is more flexible than the first material. The second material can be elastic fabric, stretch fabric, or the like. The first material can be a fabric or cotton that is more rigid than the stretch or elastic fabric.

Figure 2B:
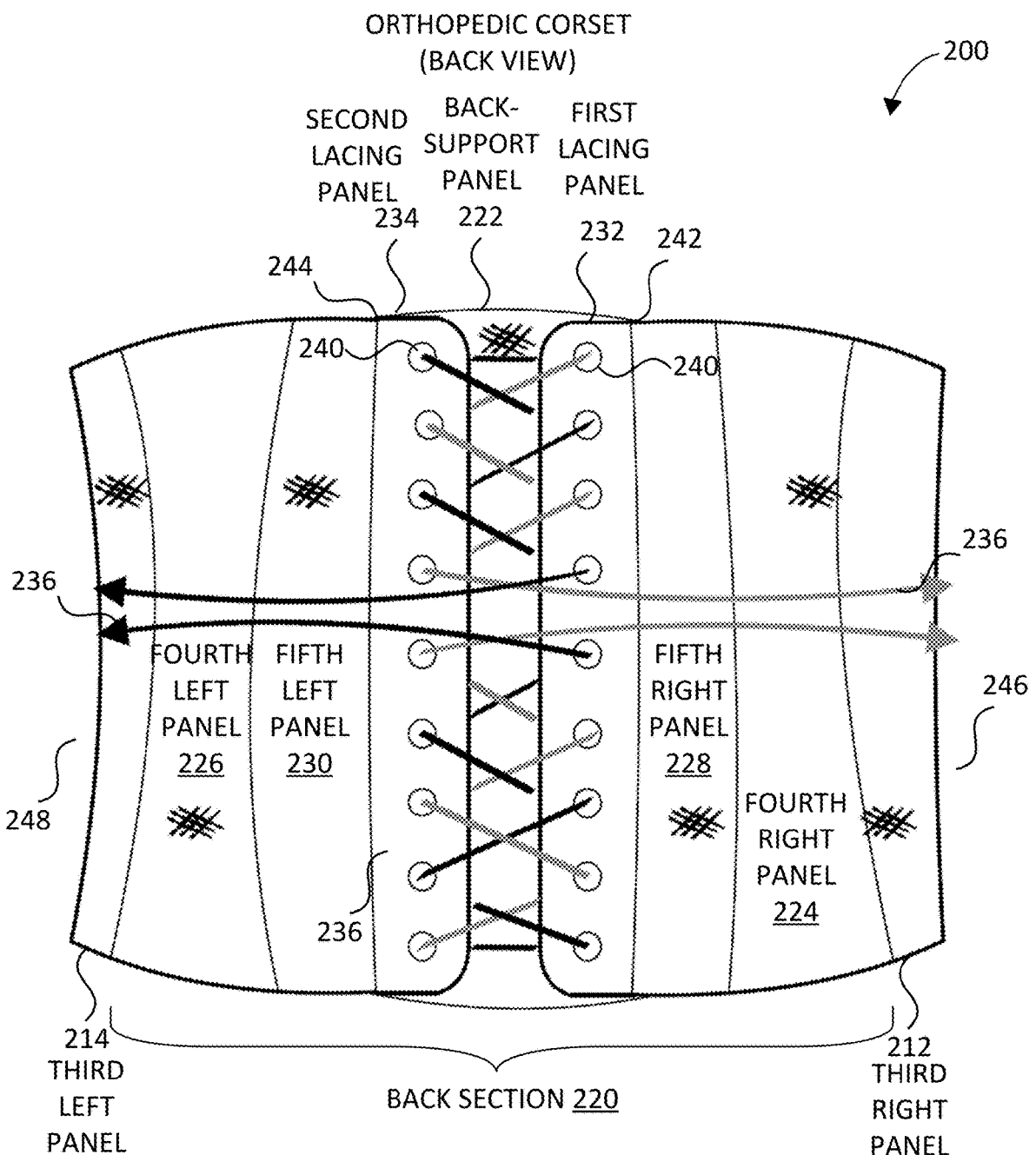
FIG. 2B illustrates a back section of the orthopedic corset of FIG. 2A according to at least one embodiment.

FIG. 2B illustrates a back section 220 of the orthopedic corset 200 of FIG. 2A according to at least one embodiment. The back section 220 includes a back-support panel 222. The back-support panel 222 is similar to the back-support panel 104 of FIG. 1B as described above, except as otherwise noted in the description. The back section 220 includes a fourth right panel 224, a fourth left panel 226, a fifth right panel 228, a fifth left panel 230, a right lacing panel 232, a left lacing panel 234, and a lacing system 236.

The fourth right panel 224 and the fifth right panel 228 are coupled together, for example, by sewing edges of the panels together at a seam. Similarly, the fourth left panel 226 and the fifth left panel 230 are coupled together, for example, by sewing edges of the panels together at a seam.

The back section 220 is coupled to two side sections. In particular, the fourth right panel 224 is coupled to the third right panel 212 on the right-side section 246 (see FIG. 2C), and the fourth left panel 226 is coupled to the third left panel 214 of the left-side section 248 (see FIG. 2D). As described above, the third right panel 212 and third left panel 214 can be flexible panels. In at least one embodiment, the panels of the back section 220 (e.g., fourth right panel 224, fourth left panel 226, fifth right panel 228, and fifth left panel 230) include outer fabric of a first material, whereas the third right panel 212 and third left panel 214 each include a fabric of a second material that is more flexible than the first material. The second material can be elastic fabric, stretch fabric, or the like. The first material can be a fabric or cotton that is more rigid than the stretch or elastic fabric.

The back-support panel 222 is coupled between the fifth right panel 228 and the fifth left panel 230. A right edge 242 of the back-support panel 222 can be sewn to a right edge of the fifth right panel 228, forming a first seam. A left edge 244 of the back-support panel 222 can be sewn to a right edge of the fifth left panel 230, forming a second seam. The right lacing panel 232 can be sewn to the back-support panel 222 and the fifth right panel 228 at the first seam. The left lacing panel 234 can be sewn to the back-support panel 222 and the fifth left panel 230 at the second seam. In other embodiments, the right lacing panel 232 and left lacing panel 234 can be sewn at different locations than the seams between the back-support panel 222 and the fifth right and left panels.

As illustrated in FIG. 2B, the back-support panel 222 is located underneath the right lacing panel 232 and left lacing panel 234. That is, the back-support panel 222 is located closer to the wearer of the orthopedic corset 200 when the orthopedic corset 200 is being worn. The back-support panel 222 can operate as a modesty panel, covering the skin or undergarment of the wearer. More importantly, the back-support panel 222 can provide orthopedic support to the wearer of the orthopedic corset 200.

Figure 2C:
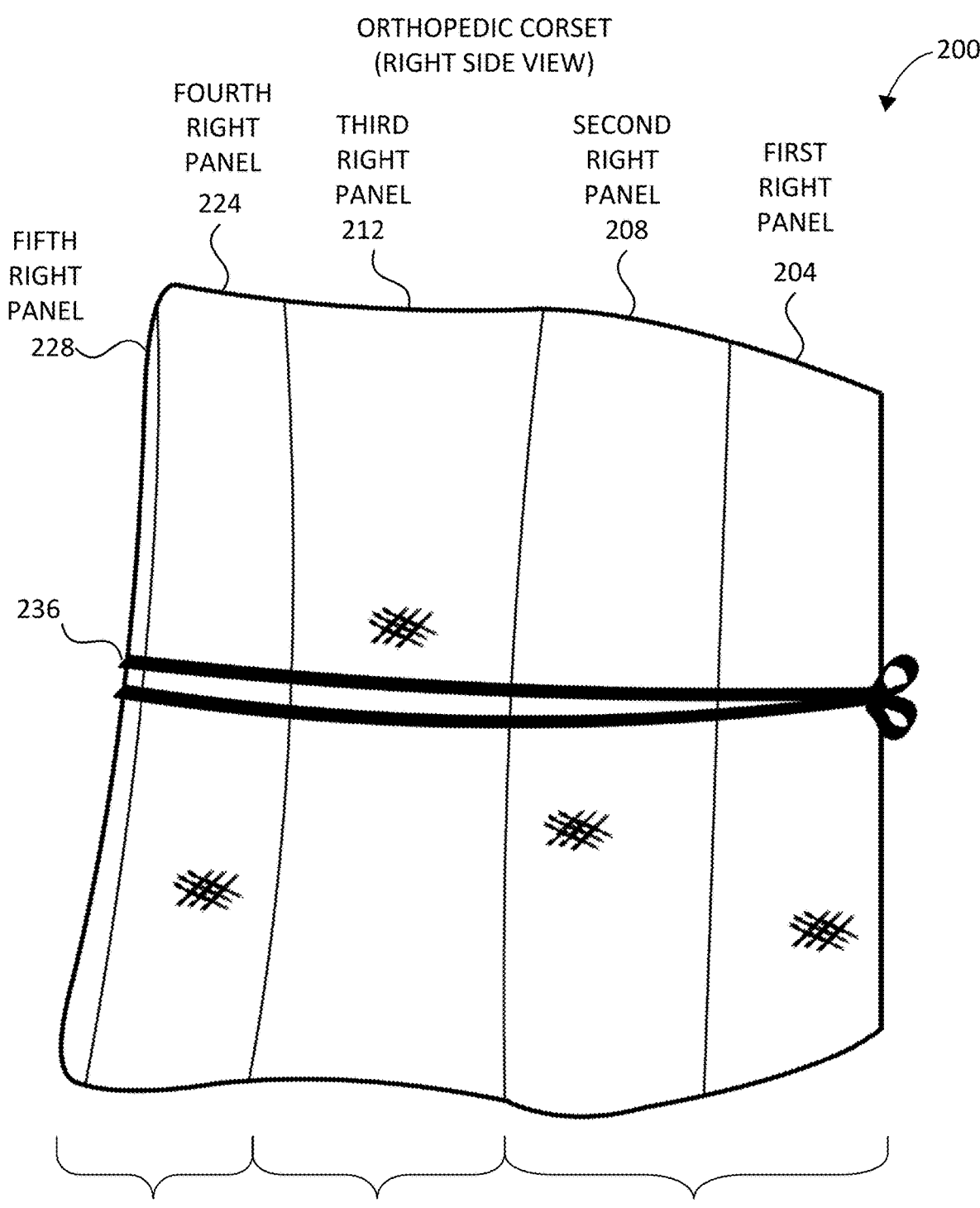
FIG. 2C illustrates a right-side section of the orthopedic corset of FIG. 2A according to at least one embodiment.

FIG. 2C illustrates the right-side section 246 of the orthopedic corset 200 of FIG. 2A according to at least one embodiment. As described above, the right-side section 246 includes the third right panel 212, which is coupled to the second right panel 208 of the front section 202 and the fourth right panel 224 of the back section 220. As described above, the third right panel 212 can be a flexible panel with flexible material, such as illustrated in FIG. 2E.

Figure 2D:
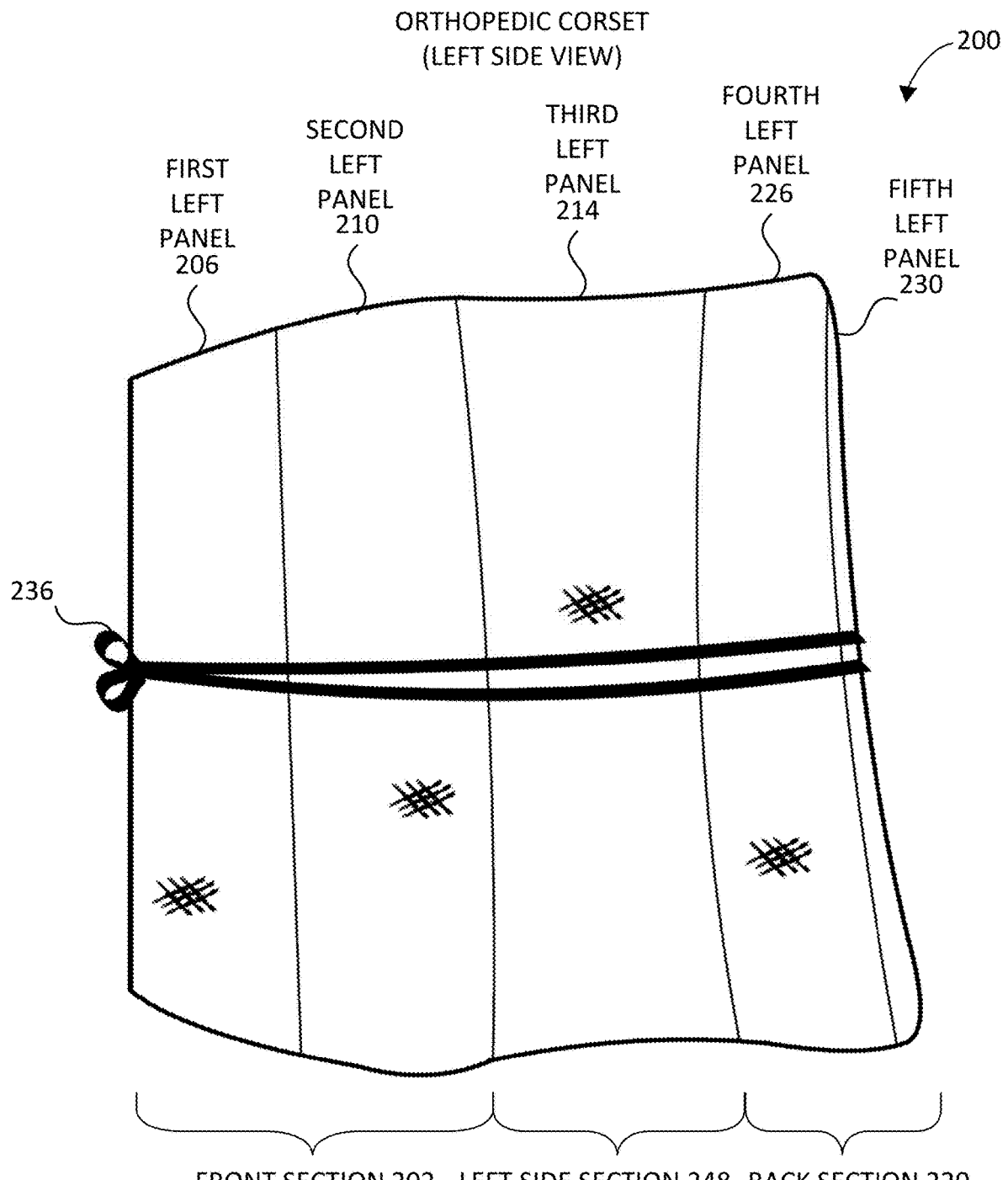
FIG. 2D illustrates a left-side section of the orthopedic corset of FIG. 2A according to at least one embodiment.

FIG. 2D illustrates the left-side section 248 of the orthopedic corset 200 of FIG. 2A according to at least one embodiment. As described above, the left-side section 248 includes the third left panel 214, which is coupled to the second left panel 210 of the front section 202 and the fourth left panel 226 of the back section 220. As described above, the third left panel 214 can be a flexible panel with flexible material, such as illustrated in FIG. 2E.

Figure 2E:
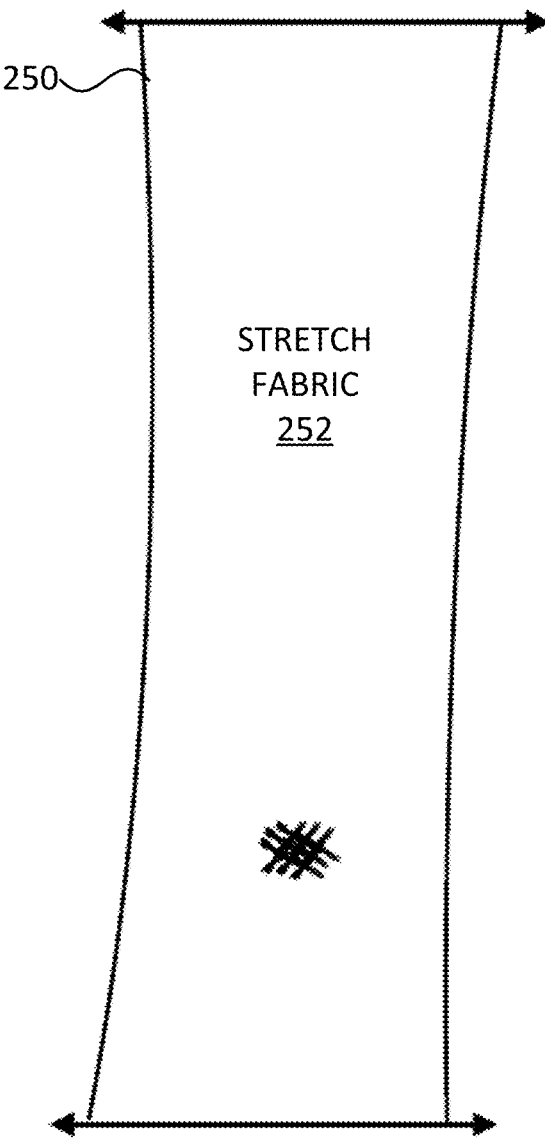
FIG. 2E illustrates a flexible panel according to at least one embodiment.

FIG. 2E illustrates a flexible panel 250 according to at least one embodiment. The flexible panel 250 includes stretch fabric 252. The flexible panel 250 can join two adjacent panels that have outer fabric that is more rigid than the stretch fabric 252. The stretch fabric 252 can stretch at least in lateral directions to provide some flexibility in the fit of the orthopedic corset 200.

As described herein, one or more panels of the orthopedic corset 200 can include one or more bonings. The bonings can be used to provide structure and shape to the orthopedic corset 200, as well as provide orthopedic support to the spine and torso of the wearer. In particular, the bonings of the back-support panel 222, and their relative placement at the back of the orthopedic corset 200 provide the orthopedic support to the wearer in a similar manner as orthopedic back straps, but as an aesthetically appealing garment.

FIG. 3A-FIG. 4A illustrate bonings, casings, and cross-sectional views of the panels with the bonings of the orthopedic corset 200 according to at least one embodiment.

Figures 3A, 3B:
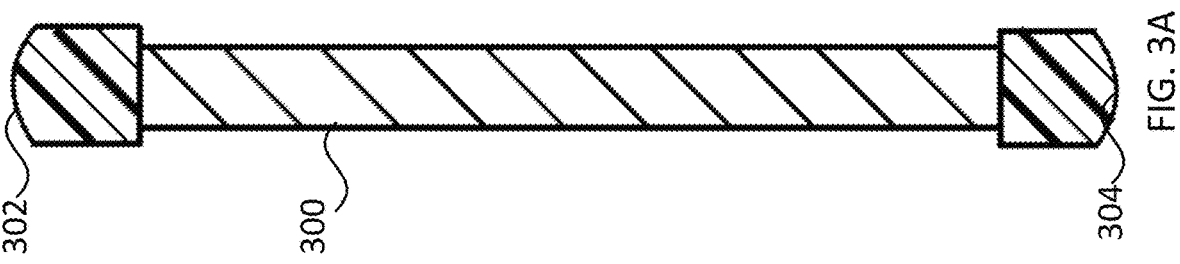
FIG. 3A illustrates a boning according to at least one embodiment.
FIG. 3B illustrates a casing in which the boning of FIG. 3A is disposed according to at least one embodiment.

FIG. 3A illustrates a boning 300 according to at least one embodiment. The boning 300 is an elongated boning that can be made of rigid or semirigid materials, such as steel, plastic, metal, animal bone material, or the like. In at least one embodiment, the boning 300 is an elongated boning of metal or plastic that is sewn in a casing that is secured to outer fabric of a panel, as illustrated in FIG. 3B. Before being sewn into a casing, a first thermoplastic material 302 is applied to a first end of the boning 300, and a second thermoplastic material 304 is applied to a second end of the boning 300. The first thermoplastic material 302 and second thermoplastic material 304 can act as barriers to prevent fabric punctures from the boning 300. In other embodiments, other bonded interfacing material can be used as the barrier. For example, the ends of the boning 300 can be coated with a coating of material that acts as the barrier.

FIG. 3B illustrates a casing 306 in which the boning 300 of FIG. 3A is disposed according to at least one embodiment. As illustrated, the boning 300 can be disposed in a casing 306. As described above, the casing 306 is a tunnel or enclosed space created in fabric for inserting the boning 300. In some cases, interfacing fabric (also referred to as "interfacing") can be bonded to an interior of the casing 306. As illustrated in an interior view of the casing, first interfacing 334 can be bonded at a top end of the casing 306 and second interfacing 336 can be bonded at a bottom end of the casing 306. The first interfacing 334 and second interfacing 336 can correspond to the first thermoplastic material 302 and second thermoplastic material 304, respectively. Bonding interface material to the fabric refers to the process of attaching interfacing to a specific part of a garment or fabric item to provide additional structure and support. When bonding interface fabric to the casing 306, an appropriate interfacing can be selected that matches the weight and type of fabric being used for the casing 306. If the casing 306 requires flexibility (like for elastic or drawstrings), a lightweight or knit interfacing may be suitable. The interfacing can be cut to the required size and shape, usually slightly smaller than the fabric piece to avoid bulk in the seam allowances. If using fusible interfacing, the adhesive side is placed against the wrong side (the non-visible side) of the fabric. It is then bonded to the fabric using an iron. The heat and pressure from the iron activate the adhesive, causing it to melt and adhere to the fabric. For sew-in interfacing, it is basted or sewn directly to the fabric. After the interfacing is attached, the fabric is then folded and sewn to create the casing 306. The first and second interfacings 334 and 336 add structure to the casing 306, making it more durable and maintaining its shape, especially important if the casing 306 will be under tension. Bonding interfacing to a casing is often done in garments where casings are used. The interfacing ensures that the casing remains stable and does not stretch out or become misshapen with use. This technique is particularly useful in garment construction to achieve a professional finish and prolong the life of the garment.

The casing 306 can be further stitched to secure the boning 300 within the fabric of the casing 306. The casing 306 can have two pieces of fabric that are sewn at the edges to create a pouch in which the boning 300 can be disposed and secured within the casing 306. The first thermoplastic material 302 and second thermoplastic material 304 disposed at the ends of the boning 300 can act as barriers to prevent the boning 300 from puncturing the fabric of the casing 306 or the fabric of the panel to which the casing 306 is secured. The first thermoplastic material 302 and second thermoplastic material 304 can also prevent the boning 300 from snagging on skin or the undergarment of the wearer. In general, the first thermoplastic material 302 and second thermoplastic material 304 can be used to prevent rough or sharp edges of the boning 300 from snagging or tearing the fabric of the casing 306, the fabric of the panel, or skin or garments of the wearer of the orthopedic corset.

As illustrated in FIG. 3C to FIG. 4A, the boning 300 can be secured to one or more panels of the orthopedic corset 200.

Figure 3C:
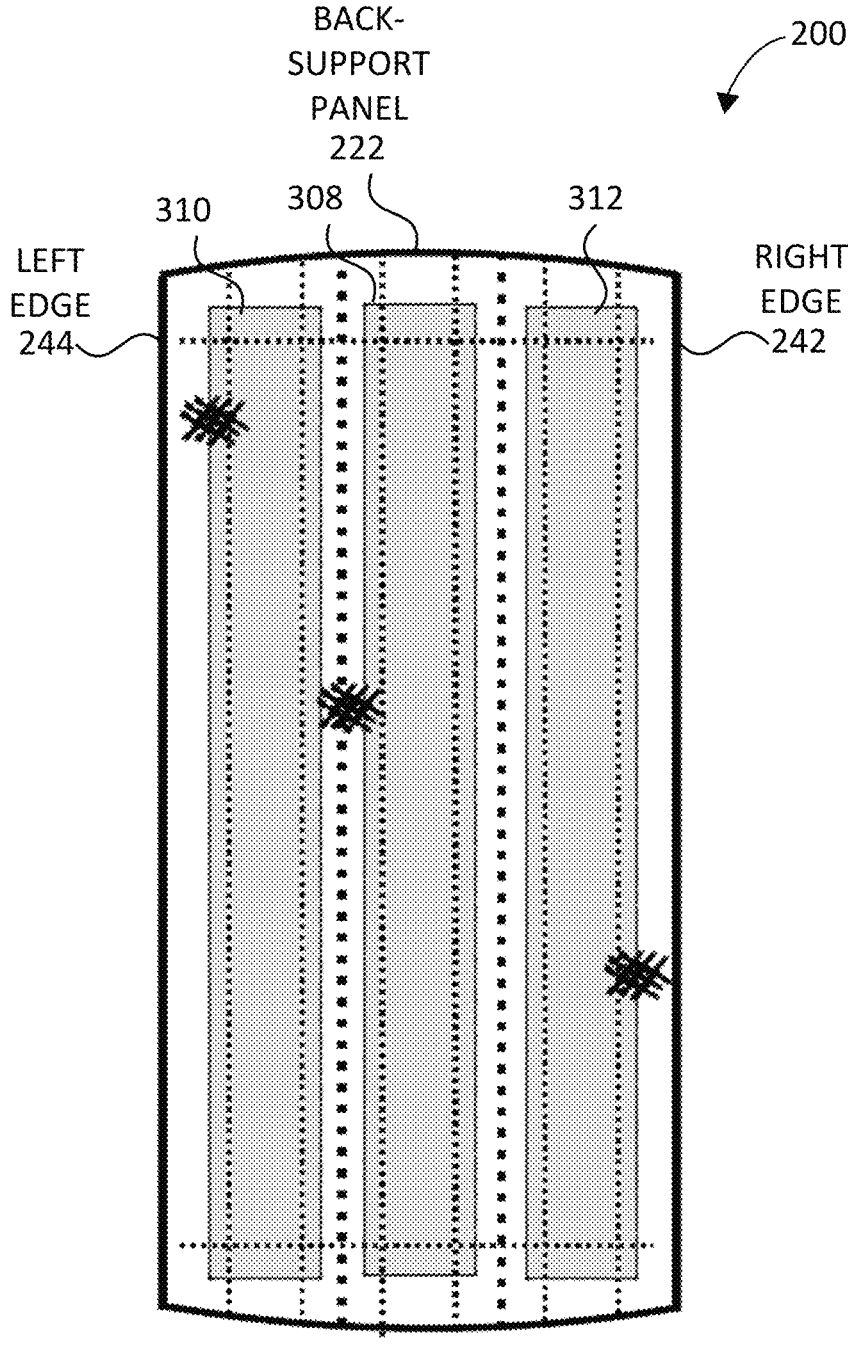
FIG. 3C is a cross-sectional view of bonings located in a back-support panel of the back section of FIG. 2A according to at least one embodiment.

FIG. 3C is a cross-sectional view of bonings located in a back-support panel 222 of the back section 220 of FIG. 2A according to at least one embodiment. In this embodiment, the back-support panel 222 includes a first boning 308, a second boning 310, and a third boning 312. The first boning 308, second boning 310, and third boning 312 are similar to the boning 300 of FIG. 3A and can include the thermoplastic material at their respective ends. Each of the first boning 308, second boning 310, and third boning 312 can be sewn into a casing, similar to casing 306 of FIG. 3A. The casing of each of the first boning 308, second boning 310, and third boning 312 can be sewn between an outer fabric and a liner of the back-support panel 222. In some embodiments, the first boning 308, second boning 310, and third boning 312 can be sewn into pouches created between the outer fabric and the liner of the back-support panel 222. For example, the three bonings can be stitched into separate channels of the back-support panel 222, one boning per channel. Although FIG. 3C illustrates three bonings in the back-support panel 222, in another embodiment, the back-support panel 222 includes four bonings. For example, the four bonings can be stitched into separate channels of the back-support panel 222, one boning per channel. In another embodiment, the back-support panel 222 includes one or more bonings.

Figure 3D:
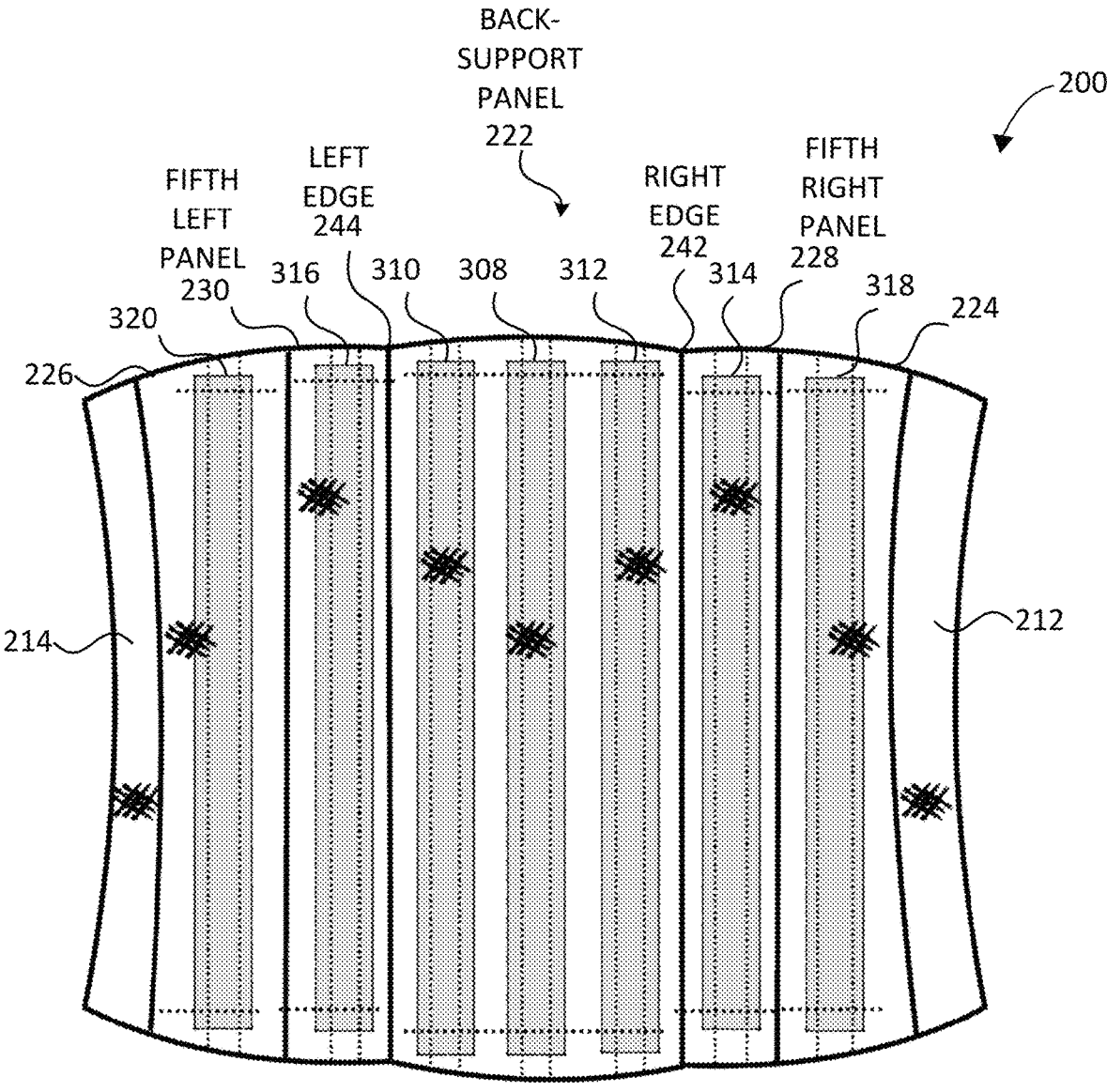
FIG. 3D is a cross-sectional view of additional bonings located in additional panels of the back section of FIG. 2A according to at least one embodiment.
Figure 3E:
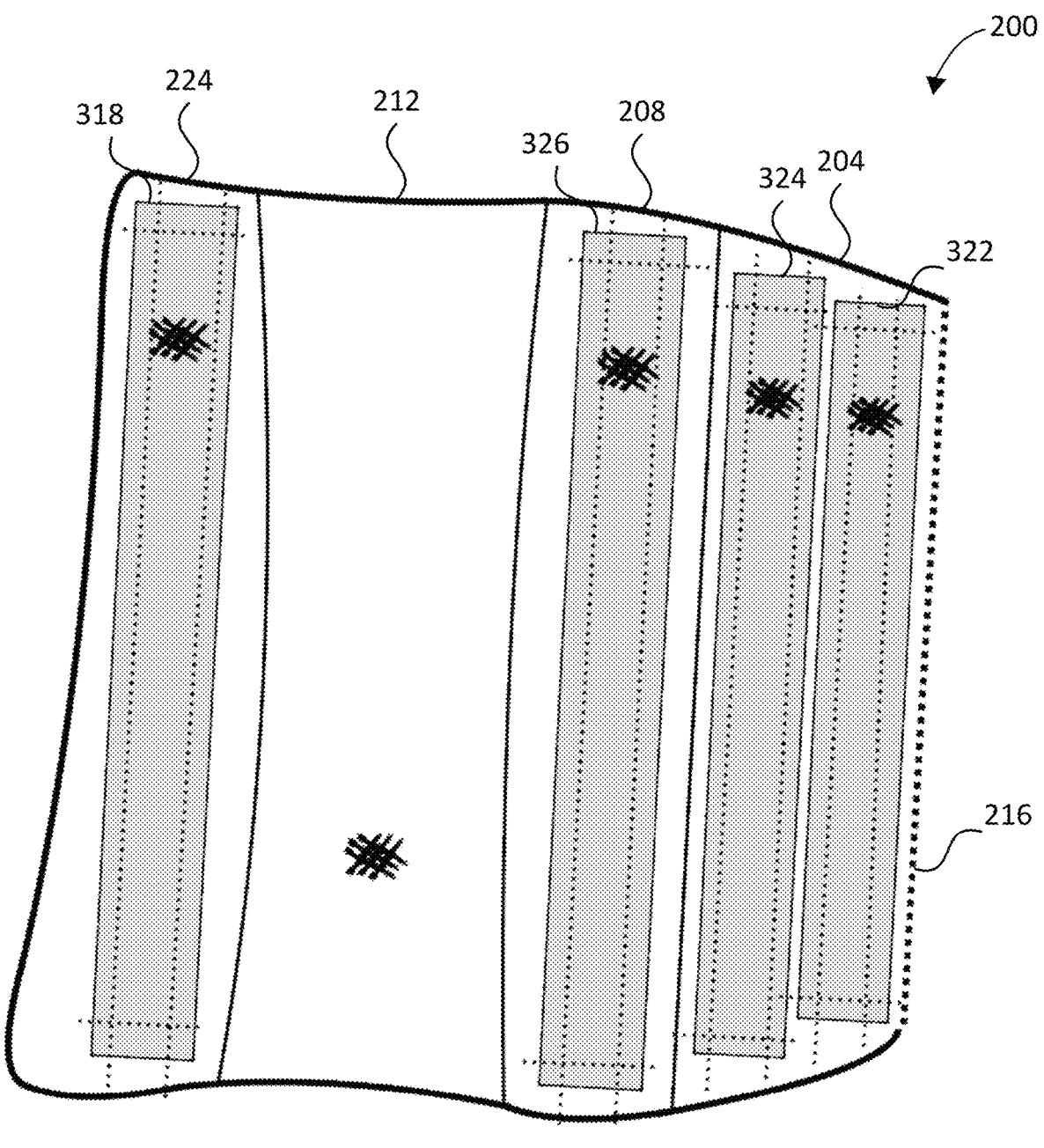
FIG. 3E is a cross-sectional view of the right-side section coupling the front section and the back section of the orthopedic corset of FIG. 2A according to at least one embodiment.
Figure 3F:
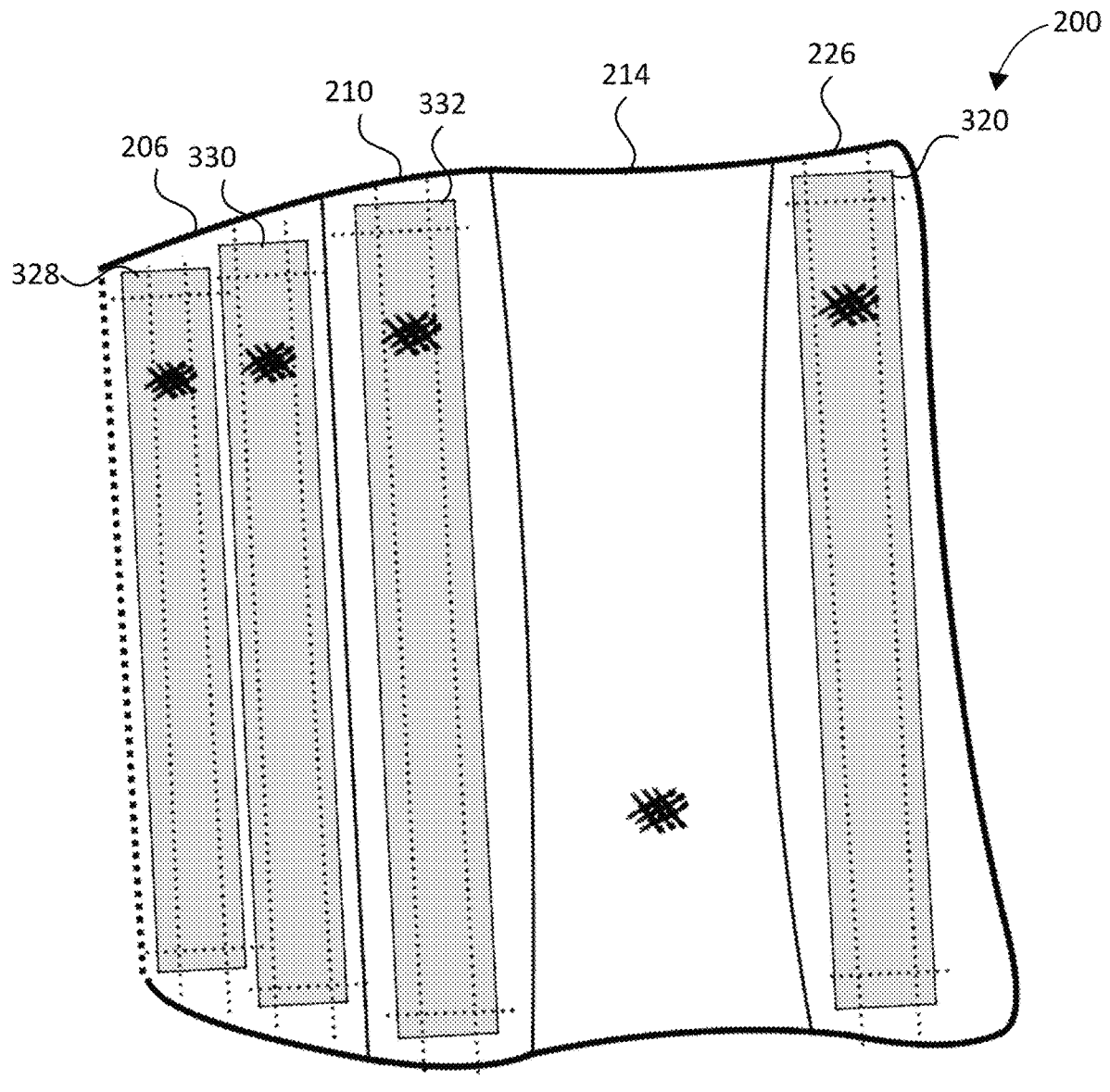
FIG. 3F is a cross-sectional view of the left-side section coupling the front section and the back section of the orthopedic corset of FIG. 2A according to at least one embodiment.
Figure 4A:
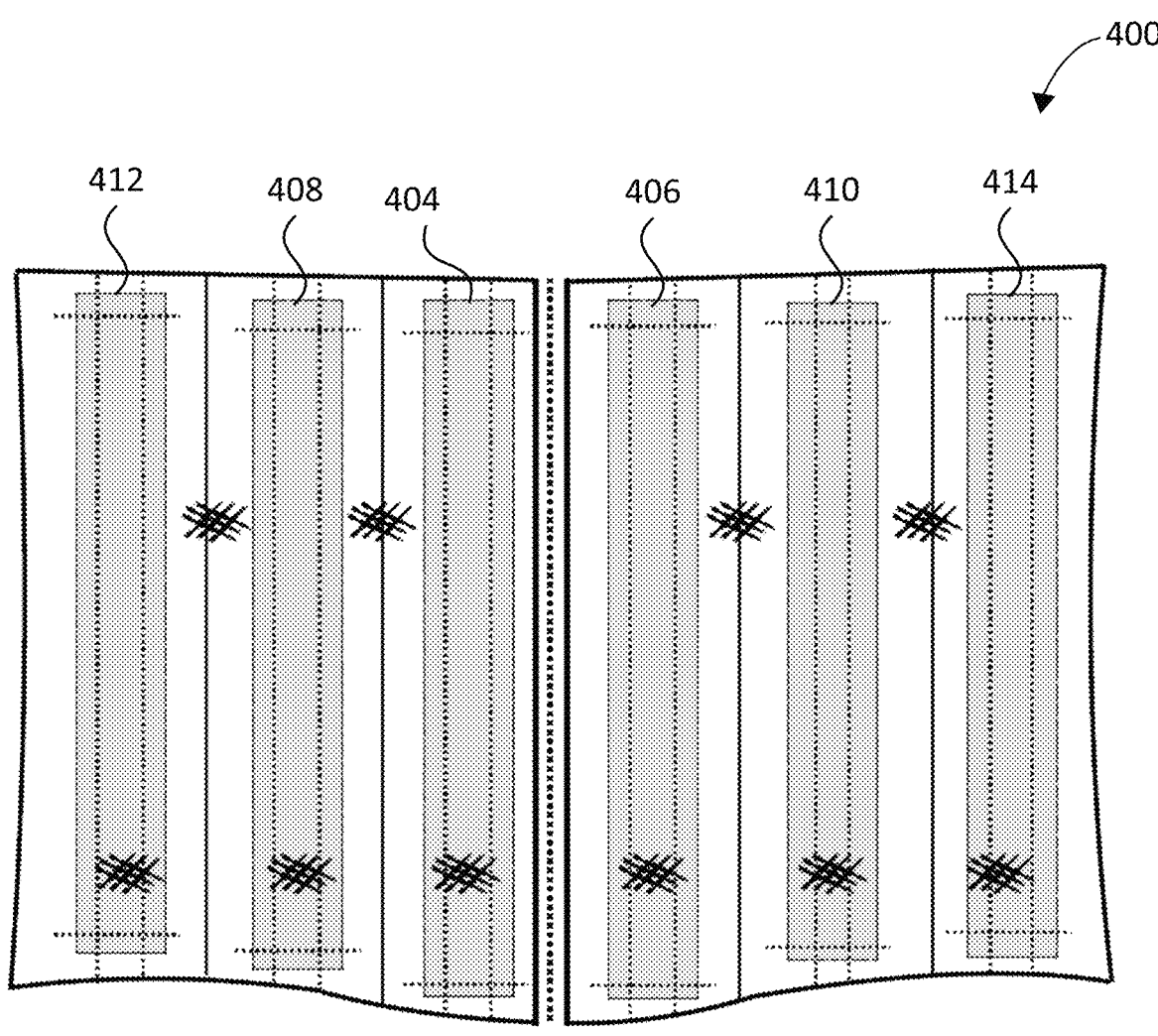
FIG. 4A is a cross-sectional view of a front section of an orthopedic corset with six panels and six bonings according to at least one embodiment.

In other embodiments, additional bonings can be added to other panels, such as the additional panels of the back section 220, such as illustrated in FIG. 3D, additional panels of the front section 202, such as illustrated in FIG. 3E, FIG. 3F, and FIG. 4A.

FIG. 3D is a cross-sectional view of additional bonings located in additional panels of the back section 220 of FIG. 2A according to at least one embodiment. As described above with respect to FIG. 3A, the back-support panel 222 includes the first boning 308, second boning 310, and third boning 312. The back-support panel 222 is coupled to the fifth right panel 228 at the right edge 242 and the fifth left panel 230 at the left edge 244. The fifth right panel 228 can include a fourth boning 314, and the fifth left panel 230 can include a fifth boning 316. The fifth right panel 228 is coupled to the fourth right panel 224 at an opposing edge of the fifth right panel 228. The fifth left panel 230 is coupled to the fourth left panel 226 at an opposing edge of the fifth left panel 230. The fourth right panel 224 can include a sixth boning 318, and the fourth left panel 226 can include a seventh boning 320. The fourth right panel 224 can be coupled to the third right panel 212 of the right-side section 246, and the fourth left panel 226 can be coupled to the third left panel 214 of the left-side section 248. Although the back section 220 is shown as having seven bonings, in other embodiments, the back section 220 can include more or less bonings than seven. In addition to the bonings in the back section 220, the orthopedic corset 200 can have additional bonings in one or more panels of the front section 202, as illustrated in FIG. 3E to FIG. 4A.

FIG. 3E is a cross-sectional view of the right-side section 246 coupling the front section 202 and the back section 220 of the orthopedic corset 200 of FIG. 2A according to at least one embodiment. The first right panel 204 of the front section 202 includes two bonings, including an eighth boning 322 and a ninth boning 324. In at least one embodiment, the eighth boning 322 can be stitched to the first right panel 204 alongside the zipper 216 to provide rigid support to the zipper 216. The second right panel 208 of the front section 202 includes one boning, including a tenth boning 326.

FIG. 3F is a cross-sectional view of the left-side section 248 coupling the front section 202 and the back section 220 of the orthopedic corset 200 of FIG. 2A according to at least one embodiment. The first left panel 206 of the front section 202 includes two bonings, including an eleventh boning 328 and a twelfth boning 330. In at least one embodiment, the twelfth boning 330 can be stitched to the first left panel 206 alongside the zipper 216 to provide rigid support to the zipper 216. The second left panel 210 of the front section 202 includes one boning, including a thirteenth boning 332.

As described herein, different numbers of panels and bonings can be used in the orthopedic corset. For example, instead of four panels in the front section of orthopedic corset 200, as illustrated in FIG. 2A, a front section can include six panels, each having a respective boning, such as illustrated in a front section 402 of an orthopedic corset 400 in FIG. 4A.

Figure 3G:
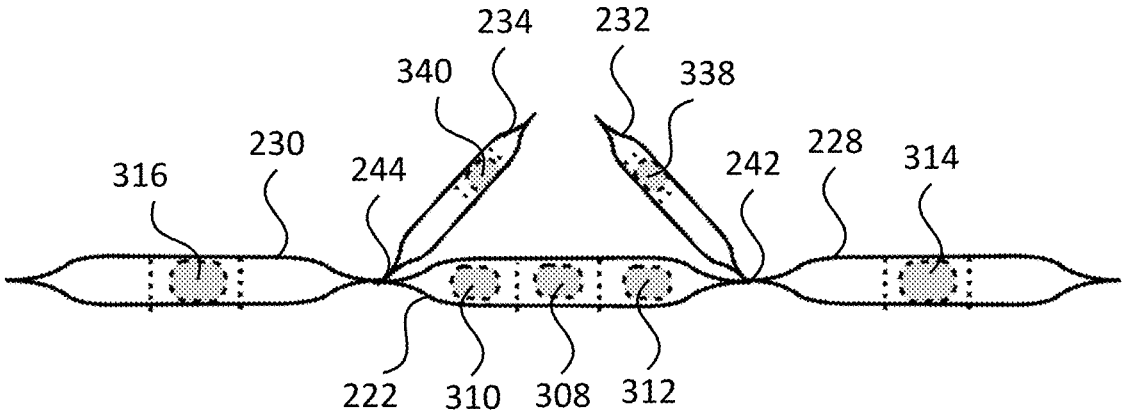
FIG. 3G is a cross-sectional view of the back-support panel of the back section of FIG. 2A according to at least one embodiment.

FIG. 3G is a cross-sectional view of the back-support panel 222 of the back section 220 of FIG. 2A according to at least one embodiment. The cross-sectional view can be a bottom view of a portion of the back section 220. As described above, the back-support panel 222 includes the first boning 308, second boning 310, and third boning 312. The right lacing panel 232 and the fifth right panel 228 are sewn to the back-support panel 222 at the right edge 242 of the back-support panel 222. The left lacing panel 234 and the fifth left panel 230 are sewn to the back-support panel 222 at the left edge 244 of the back-support panel 222. For additional support, the right lacing panel 232 can include a fourteenth boning 338, and the left lacing panel 234 can include a fifteenth boning 340. The fourteenth boning 338 and fifteenth boning 340 can be located between reinforcement rings and the opposing edges of the right lacing panel 232 and left lacing panel 234.

FIG. 4A is a cross-sectional view of a front section 402 of an orthopedic corset 400 with six panels and six bonings according to at least one embodiment. The orthopedic corset 400 includes six panels, three panels on the right and three panels on the left. The orthopedic corset 400 includes six bonings, including first boning 404, second boning 406, third boning 408, fourth boning 410, fifth boning 412, sixth boning 414. As illustrated in FIG. 4A, there is one boning per panel. In other embodiments, each panel can include zero or more bonings.

Figure 4B:
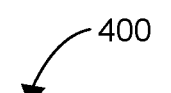
FIG. 4B illustrates a front view of the front section of the orthopedic corset of FIG. 4A according to at least one embodiment.
Figure 4B:
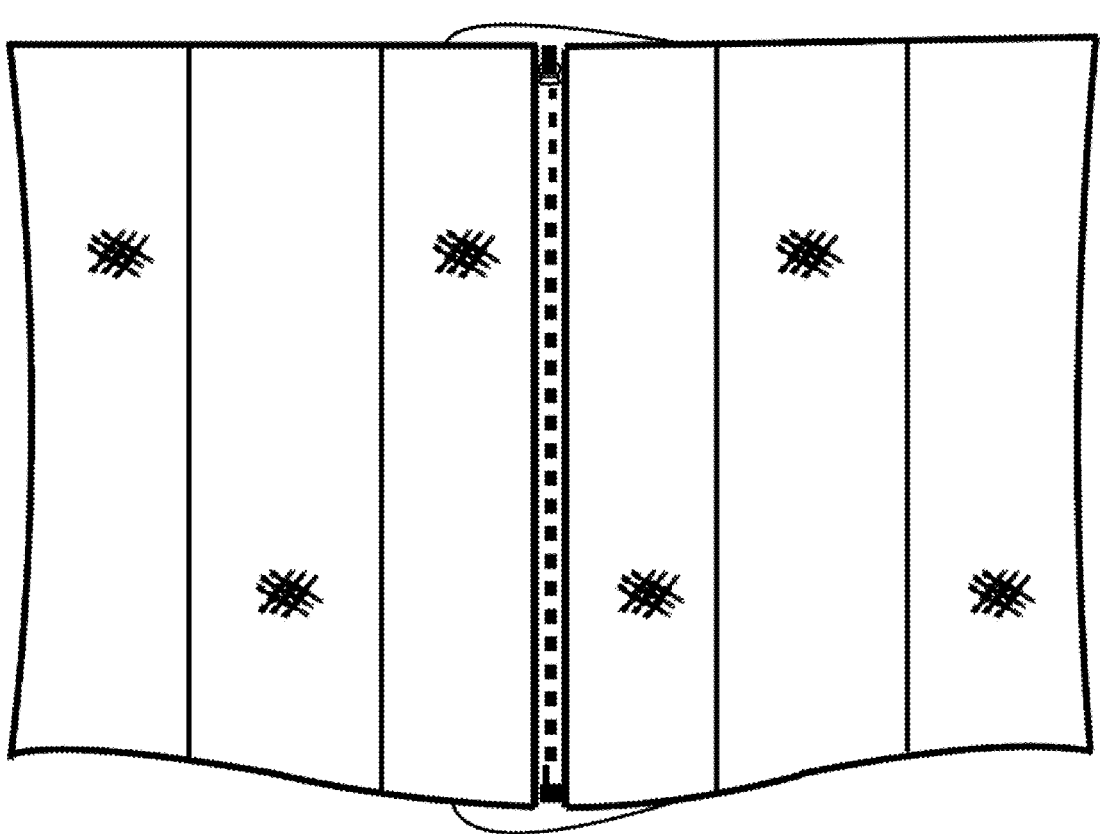

FIG. 4B illustrates a front view of the front section 402 of the orthopedic corset 400 according to at least one embodiment. As illustrated in the front view (or exterior view) of the front section 402, the orthopedic corset 400 includes a zipper 416 and a zipper shield 418 located behind the zipper 416.

Figure 4C:
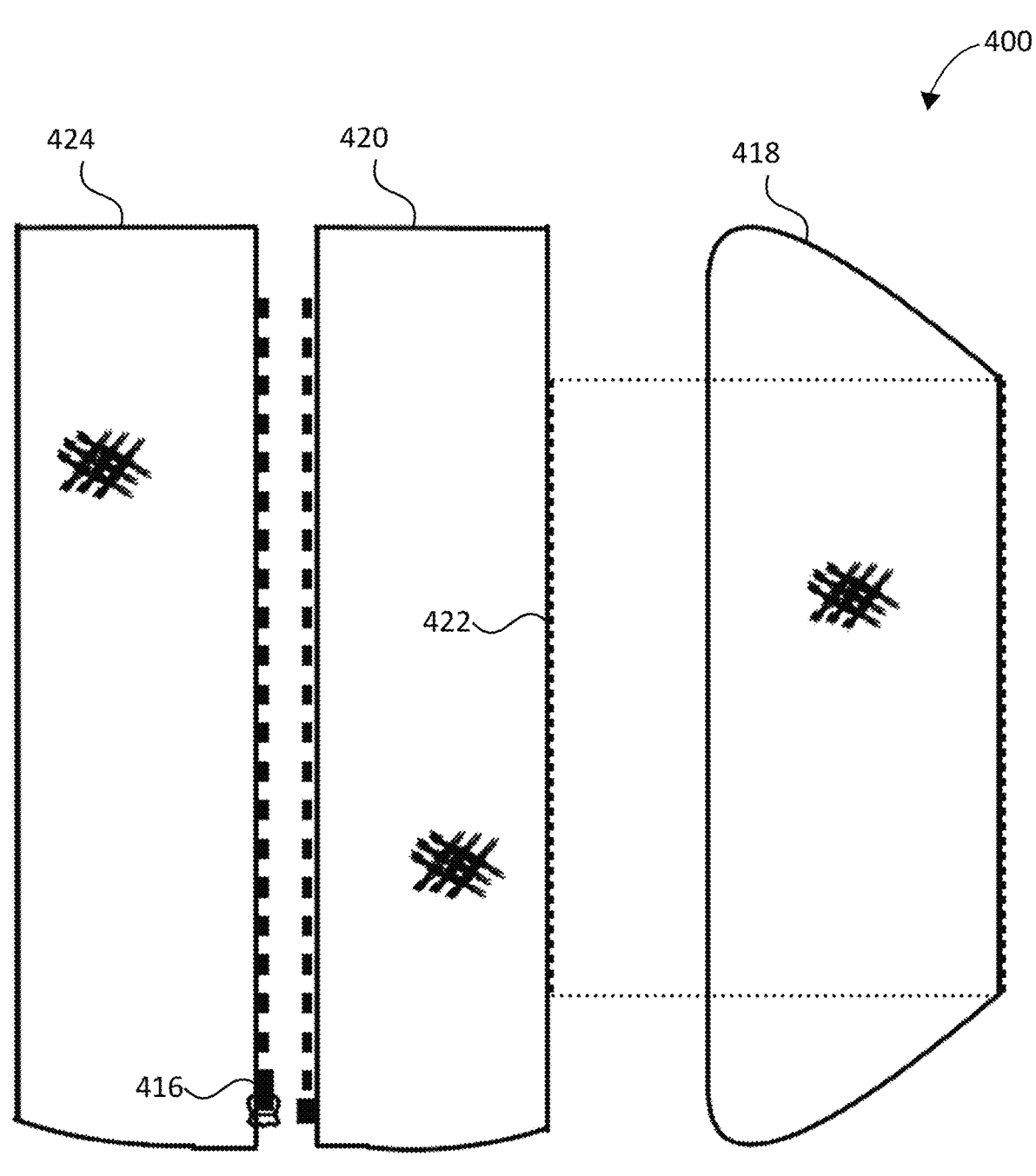
FIG. 4C illustrates a rear view of the front section of the orthopedic corset of FIG. 4A according to at least one embodiment.

FIG. 4C illustrates a rear view of the front section of the orthopedic corset of FIG. 4A according to at least one embodiment. As illustrated in the rear view (or interior view) of the front section 402, the zipper shield 418 can be stitched to a panel 420 of the orthopedic corset 400 at a seam 422. It should be noted that the zipper shield 418 can be stitched to an opposing panel 424 in other embodiments.

Figure 5A:
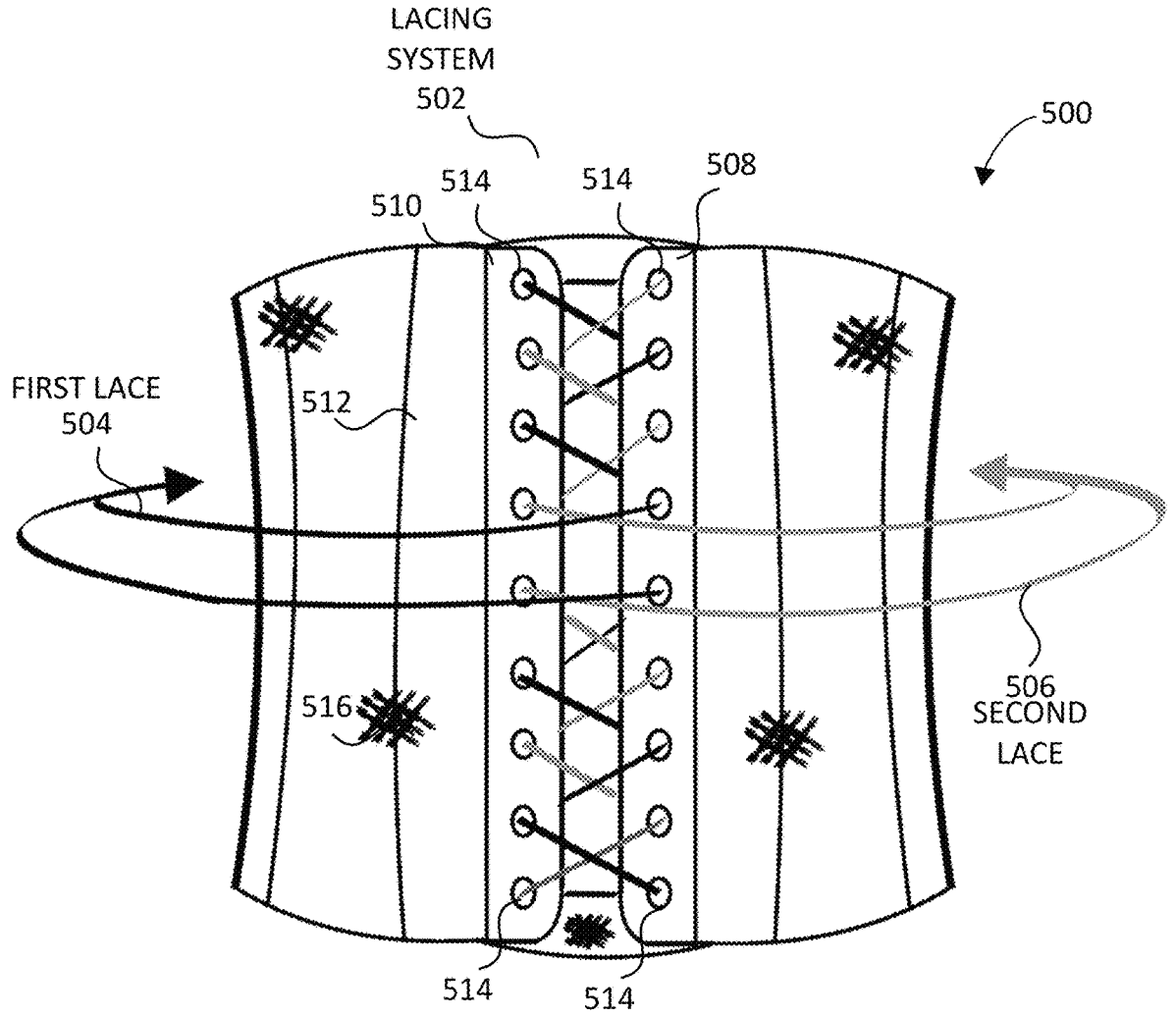
FIG. 5A-FIG. 5B illustrate an orthopedic corset 500 with a lacing system 502 for adjusting a tightness of the orthopedic corset 500 from a front side of the orthopedic corset 500 according to at least one embodiment.
Figure 5B:
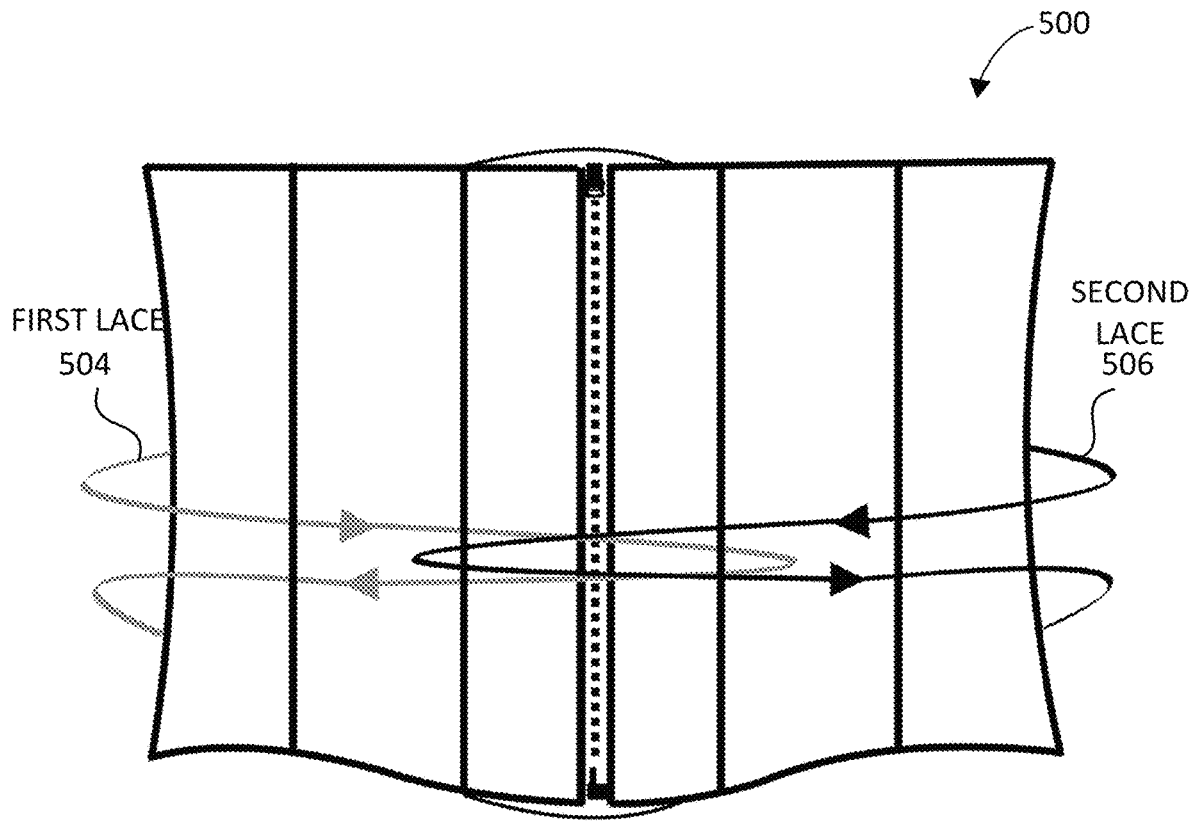

FIG. 5A-FIG. 5B illustrate an orthopedic corset 500 with a lacing system 502 for adjusting a tightness of the orthopedic corset 500 from a front side of the orthopedic corset 500 according to at least one embodiment. The lacing system 502 includes a first lace 504 (i.e., a first cord) and a second lace 506 (i.e., a second cord). The first lace 504 and second lace 506 can be equal in length. There are a first set of reinforcement rings 514 located on the first lacing panel 508 and a second set of reinforcement rings 514 located on the second lacing panel 510. The first lace 504 is laced through alternating ones of the first set and the second set of reinforcement rings, and a second lace 506 is laced through alternating ones of the first set and the second set of reinforcement rings 514. Each pair of opposing reinforcement rings 514 of the first set and the second set of reinforcement rings 514 provides a point of adjustment for tightening or loosening the orthopedic corset 500. The first lace 504 and the second lace 506 each has a length to extend from the back section to the front section to permit a person wearing the orthopedic corset 500 to secure the first lace 504 and the second lace 506 at a front side of the orthopedic corset 500.

In at least one embodiment, a first end of each of the first lace 504 and second lace 506 is sewn to a top end of a lacing panel (e.g., lacing panels 508 and 510, respectively). The first lace 504 and second lace 506 are laced diagonally through opposing reinforcement rings 514 in the lacing panels 508 and 510 into a center of the orthopedic corset 500. The first lace 504 and second lace 506 are extended on opposing sides to reach around to the front side of the orthopedic corset 500. The first lace 504 and second lace 506 can be continued to be laced diagonally to a bottom end of the lacing panels 508 and 510. A second end of each of the first lace 504 and second lace 506 is sewn to a bottom end of the respective lacing panel (e.g., lacing panels 508 and 510, respectively).

In another embodiment, the lacing system 502 uses a single cord. The single cord can be laced by sewing a first end at a top end of the lacing panel 508, lacing diagonally downwards through opposing rings to the two center reinforcement rings 514. On the lacing panel 510, the single cord can be extended to reach around to the front side of the orthopedic corset 500. The single cord can be continued to be laced diagonally to the bottom reinforcement ring 514, and then laced diagonally upwards to two center rings on the lacing panel 508 where the cord is extended to reach around to the corset front, continue to lace diagonally upwards to the top of the second lacing panel; and then sew a second end of the cord to a top end of the lacing panel 510.

In another embodiment, the lacing system 502 can be implemented with a dual-level tightening system with one lace that starts at the top and one lace that starts at the bottom and meet in the middle and then extend to the front side for tightening by the wearer. The lacing system 502 allows a wearer to apply the orthopedic corset 500 without the assistance of another person by the inclusion of rear cinching that allows the wearer to tighten the orthopedic corset 500 around the lower torso from the front of the orthopedic corset 500. The wearer can adjust the lacing system 502 to a suitable comfort level determined by the wearer, providing lower torso support and a slenderizing effect while not restricting general lumbar movement and flexibility.

The lacing system 502 can be implemented in other manners than those described above.

Figure 6A:
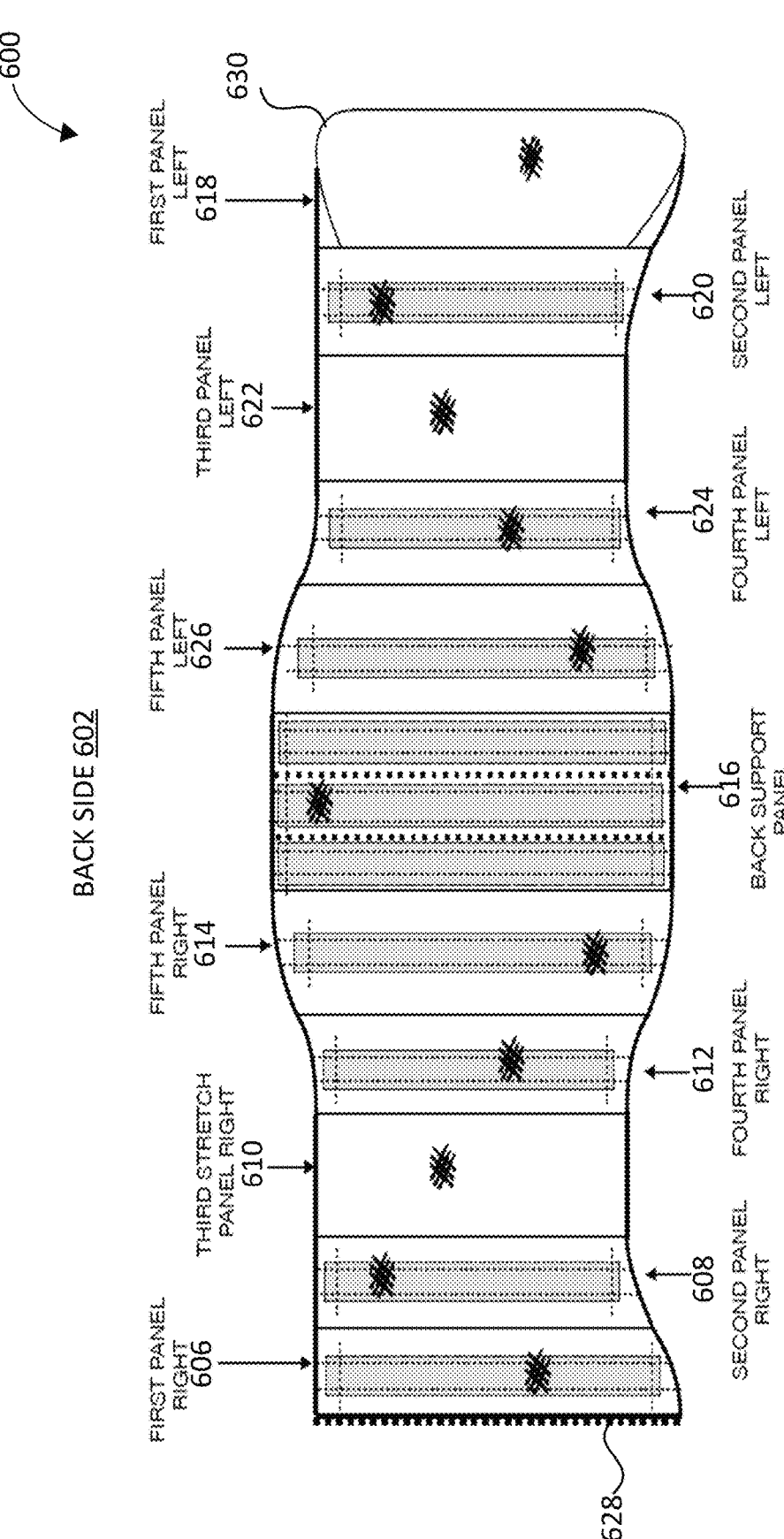
FIG. 6A illustrates an aspect of the subject matter in accordance with one embodiment.

FIG. 6A illustrates a cross-sectional view of a back side 602 of an orthopedic corset 600 according to at least one embodiment. The back side 602 includes a first panel 606 (right), a second panel 608 (right) coupled to the first panel 606, a third stretch panel 610 (right) coupled to the second panel 608, a fourth panel 612 (right) coupled to the third stretch panel 610, a fifth panel 614 (right) coupled to the fourth panel 612, a back-support panel 616 coupled to the fifth panel 614. The back side 602 also includes a first panel 618 (left), a second panel 620 (left) coupled to the first panel 618, a third panel 622 (left) coupled to the second panel 620, a fourth panel 624 (left) coupled to the third panel 622, a fifth panel 626 (left) coupled to the fourth panel 624 and the back-support panel 616. The orthopedic corset 600 can include a zipper 628 and a zipper shield 630, similar to the zipper shield 218 and zipper shield 418 described above. The back-support panel 616 can include three bonings. The fifth panel 614 and fifth panel 626 can each include a boning. The fourth panel 612 and fourth panel 624 can each include a boning. The second panel 608 and second panel 620 can each include a boning. The first panel 606 and first panel 618 can each include a boning. The boning of the first panel 618 and the portion of the zipper 628 are obscured by the zipper shield 630 in FIG. 6A. The panels and bonings of FIG. 6A are similar to the panels and bonings described above.

Figure 6B:
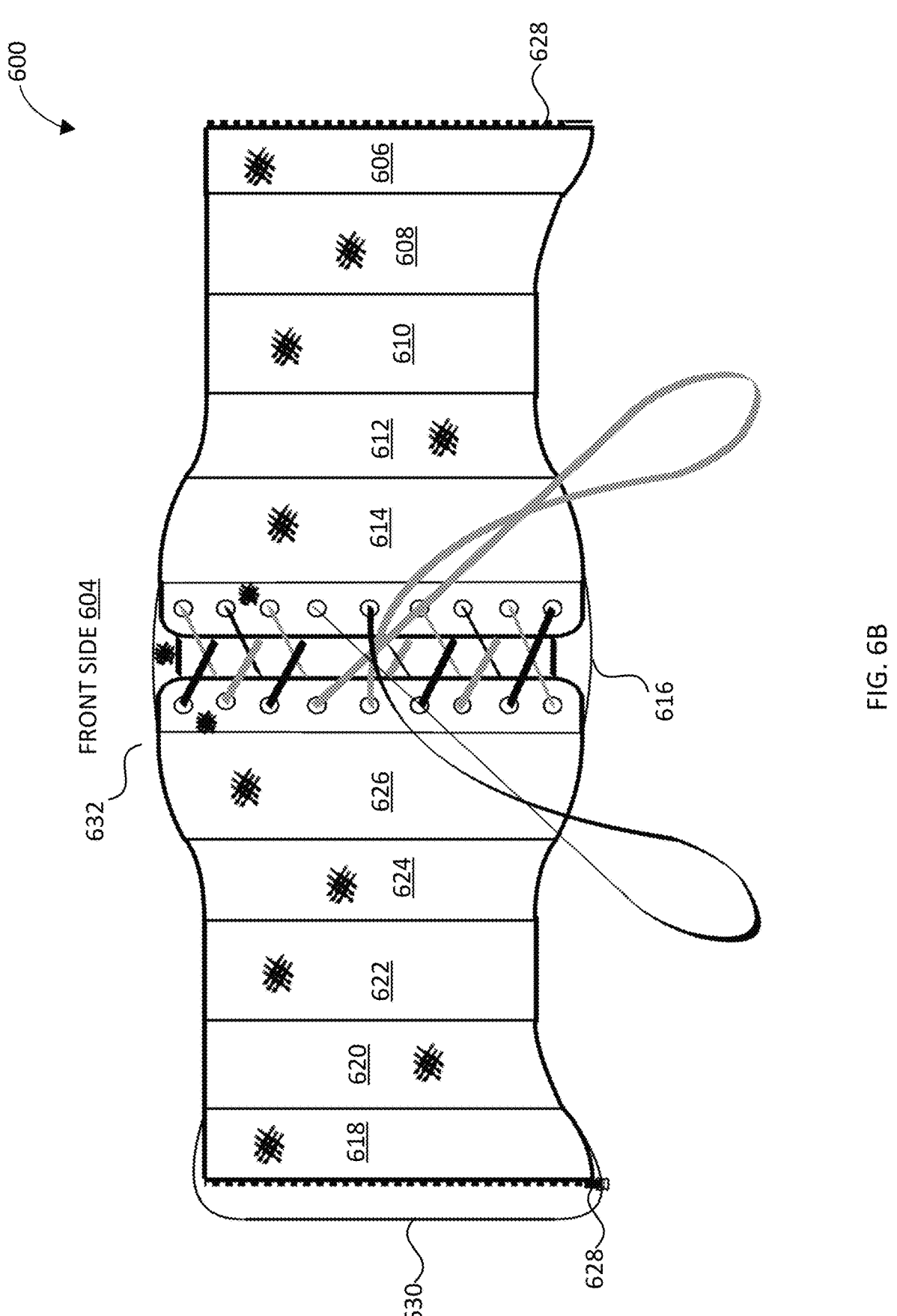
FIG. 6B illustrates an aspect of the subject matter in accordance with one embodiment.

FIG. 6B illustrates a front view of a front side 604 of the orthopedic corset 600 of FIG. 6A according to at least one embodiment. The front view shows the first panel 606 (right), second panel 608 (right), third stretch panel 610 (right), fourth panel 612 (right), fifth panel 614 (right), back-support panel 616, first panel 618 (left), second panel 620 (left), third panel 622 (left), fourth panel 624 (left), fifth panel 626 (left), zipper 628, and zipper shield 630. The front view also illustrates a lacing system 632. The lacing system 632 can be similar to the lacing system 502 described above.

FIG. 7 illustrates a method of manufacturing an orthopedic corset according to at least one embodiment. At block 702, method 700 sews tape of a zipper into a right edge of a first right panel and a right edge of a first left panel to permit the zipper to fasten the first right panel and the first left panel at a front side of the orthopedic corset. At block 704, method 700 disposes a first thermoplastic material on a first end of an elongated boning. At block 706, method 700 disposes a second thermoplastic material on a second end of the elongated boning. At block 708, method 700 sews a casing comprising the elongated boning. At block 710, method 700 sews the casing in a back-support panel. At block 712, method 700 sews a right edge of the back-support panel, a right edge of a first lacing panel, and a right edge of a second right panel at a first seam at a back side of the orthopedic corset. At block 714, method 700 sews a left edge of the back-support panel, a right edge of a second lacing panel, and a right edge of a second left panel at a second seam at the back side of the orthopedic corset.

Various operations of method 700 may be performed differently than the order shown in FIG. 7. Some operations of the methods may be performed concurrently with other operations. In at least one embodiment, one or more operations shown in FIG. 7 may not always be performed. In at least one embodiment, additional operations than those shown in FIG. 7 may also be performed.

Other variations are within the spirit of the present disclosure. Thus, while disclosed techniques are susceptible to various modifications and alternative constructions, certain illustrated embodiments thereof are shown in drawings and have been described above in detail. It should be understood, however, that there is no intention to limit the disclosure to a specific form or forms disclosed, but on the contrary, the intention is to cover all modifications, alternative constructions, and equivalents falling within the spirit and scope of the disclosure, as defined in appended claims.

Use of terms "a" and "an" and "the" and similar referents in the context of describing disclosed embodiments (especially in the context of following claims) are to be construed to cover both singular and plural, unless otherwise indicated herein or clearly contradicted by context, and not as a definition of a term. Terms "comprising," "having," "including," and "containing" are to be construed as open-ended terms (meaning "including, but not limited to,") unless otherwise noted. The term "connected," when unmodified and referring to physical connections, is to be construed as partly or wholly contained within, attached to, or joined together, even if there is something intervening. Recitations of ranges of values herein are merely intended to serve as a shorthand method of referring individually to each separate value falling within range unless otherwise indicated herein, and each separate value is incorporated into the specification as if it were individually recited herein. Use of the term "set" (e.g., "a set of items") or "subset," unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but subset and corresponding set may be equal.

Conjunctive language, such as phrases of the form "at least one of A, B, and C," or "at least one of A, B, and C," unless specifically stated otherwise or otherwise clearly contradicted by context, is otherwise understood with the context as used in general to present that an item, term, etc., may be either A or B or C, or any nonempty subset of a set of A and B and C. For instance, in the illustrative example of a set having three members, conjunctive phrases "at least one of A, B, and C" and "at least one of A, B, and C" refers to any of the following sets: {A}, {B}, {C}, {A, B}, {A, C}, {B, C}, {A, B, C}. Thus, such conjunctive language is not generally intended to imply that certain embodiments require at least one of A, at least one of B, and at least one of C each to be present. In addition, unless otherwise noted or contradicted by context, the term "plurality" indicates a state of being plural (e.g., "a plurality of items" indicates multiple items). A plurality is at least two items but can be more when so indicated either explicitly or by context. Further, unless stated otherwise or otherwise clear from context, the phrase "based on" means "based at least in part on" and not "based solely on."

Use of any and all examples, or exemplary language (e.g., "such as") provided herein, is intended merely to better illuminate embodiments of the disclosure and does not pose a limitation on the scope of the disclosure unless otherwise claimed. No language in the specification should be construed as indicating any non-claimed element as essential to the practice of the disclosure.

The terms "coupled" and "connected," along with their derivatives, may be used in the description and claims. It should be understood that these terms may not be intended as synonyms for each other. Rather, in particular examples, "connected" or "coupled" may be used to indicate that two or more elements are in direct or indirect physical contact with each other. "Coupled" may also mean that two or more elements are not in direct contact with each other but yet still co-operate or interact with each other.

Although the discussion above sets forth example implementations of described techniques, other architectures may be used to implement the described functionality and are intended to be within the scope of this disclosure. Furthermore, although specific distributions of responsibilities are defined above for purposes of discussion, various functions and responsibilities might be distributed and divided in different ways, depending on circumstances.

Furthermore, although the subject matter has been described in language specific to structural features and/or methodological acts, it is to be understood that the subject matter claimed in appended claims is not necessarily limited to specific features or acts described. Rather, specific features and acts are disclosed as exemplary forms of implementing the claims.

What is claimed is:
1. An orthopedic corset comprising:
a front section having a first right panel and a first left panel;
a zipper to fasten the first right panel and the first left panel;
a zipper shield coupled to one of the first right panel or the first left panel, wherein the zipper shield is located behind the zipper when the zipper is closed to prevent direct contact between skin or undergarments and the zipper;
a back section;
a right-side section coupled between the front section and the back section on a right side of the orthopedic corset;
a left-side section coupled between the front section and the back section on a left side of the orthopedic corset, wherein the back section comprises:
a second right panel coupled to the right-side section;
a third right panel coupled to the second right panel, wherein at least one of the second right panel or the third right panel comprises a first boning;
a second left panel coupled to the left-side section;
a third left panel coupled to the second left panel, wherein at least one of the second left panel or the third left panel comprises a second boning;
a back-support panel coupled to the third right panel and the third left panel, the back-support panel comprising one or more bonings, wherein at least one of the one or more bonings comprises a steel boning that flexes in two or more directions;
a lacing system to adjust a tightness of the orthopedic corset, the lacing system comprising:
a first lacing panel coupled to the third right panel or the back-support panel;
a second lacing panel coupled to the third left panel or the back-support panel, wherein the back-support panel is located behind the first lacing panel and the second lacing panel;
a first set of reinforcement rings located on the first lacing panel;
a second set of reinforcement rings located on the second lacing panel;
a first lace laced through alternating ones of the first set and the second set of reinforcement rings; and
a second lace laced through alternating ones of the first set and the second set of reinforcement rings.

2. The orthopedic corset of claim 1, wherein:

the first lacing panel and the third right panel are coupled to the back-support panel at a right edge of the back-support panel; and the second lacing panel and the third left panel are coupled to the back-support panel at a left edge of the back-support panel.

3. The orthopedic corset of claim 1, wherein at least one of the first boning, the second boning, or the one or more bonings comprises a spiral steel boning that flexes in two or more directions.

4. The orthopedic corset of claim 1, wherein at least one of the first boning, the second boning, or the one or more bonings comprises a steel boning that flexes in only two directions.

5. The orthopedic corset of claim 1, wherein at least one of the first boning or the second boning comprises a plastic boning.

6. The orthopedic corset of claim 1, wherein the at least one of the one or more bonings comprises:

a first thermoplastic material disposed on a first end of the steel boning; and a second thermoplastic material disposed on a second end of the steel boning.

7. The orthopedic corset of claim 1, wherein the back-support panel comprises an outer fabric and a liner, wherein each of the one or more bonings is disposed in a casing that is disposed between the outer fabric and the liner.

8. The orthopedic corset of claim 7, wherein the casing comprises interfacing bonded to the casing.

9. The orthopedic corset of claim 1, wherein panels of the front section and the back section comprise outer fabric of a first material, wherein the right-side section and the left-side section each comprises a fabric of a second material that is more flexible than the first material.

10. The orthopedic corset of claim 1, wherein the back-support panel comprises three or four bonings.

11. The orthopedic corset of claim 1, further comprising two of additional bonings disposed in the first right panel and the first left panel.

12. The orthopedic corset of claim 1, wherein:

the back-support panel comprises a first outer fabric; and the first lacing panel and the second lacing panel each comprises a second outer fabric, wherein the first outer fabric is more flexible than the second outer fabric.

13. The orthopedic corset of claim 1, wherein:

each pair of opposing reinforcement rings of the first set and the second set of reinforcement rings provide a point of adjustment for tightening or loosening the orthopedic corset; and the first lace and the second lace each has a length to extend from the back section to the front section to permit a person wearing the orthopedic corset to secure the first lace and the second lace at a front side of the orthopedic corset.

14. An orthopedic corset comprising:

a first panel;

a second panel;

a zipper to fasten the first panel and the second panel at a front side of the orthopedic corset;

a zipper shield located behind the zipper when the zipper is closed to prevent direct contact between skin or undergarments and the zipper;

a third panel located at a back side of the orthopedic corset;

a fourth panel located at the back side of the orthopedic corset;

a fifth panel located at the back side of the orthopedic corset, wherein a first boning is disposed in the third panel or the fifth panel;

a sixth panel located at the back side of the orthopedic corset, wherein a second boning is disposed in the fourth panel or the sixth panel;

a lacing system at the back side of the orthopedic corset, the lacing system to adjust a tightness of the orthopedic corset; and a back-support panel coupled between the third panel and the fourth panel, the back-support panel being located behind the lacing system, and the back-support panel comprising one or more steel bonings that flex in two or more directions, wherein the lacing system comprises:

a first set of reinforcement rings located on a first lacing panel;

a second set of reinforcement rings located on a second lacing panel;

a first lace laced through alternating ones of the first set and the second set of reinforcement rings; and a second lace laced through alternating ones of the first set and the second set of reinforcement rings.

15. The orthopedic corset of claim 14, further comprising one or more additional bonings disposed in at least one of the first panel, the second panel, the other one of the third panel or the fifth panel, or the other one of the fourth panel or sixth panel.

16. The orthopedic corset of claim 14, wherein the one or more steel bonings comprises a spiral steel boning that flexes in two or more directions.

17. The orthopedic corset of claim 14, wherein the one or more steel bonings flex in only two directions.

18. A method of manufacturing an orthopedic corset, the method comprising:

sewing tape of a zipper into a first edge of a first right panel and a first edge of a first left panel to permit the zipper to fasten the first right panel and the first left panel at a front side of the orthopedic corset;

sewing a zipper shield to one of the first right panel or the first left panel, wherein the zipper shield is located behind the zipper when the zipper is closed to prevent direct contact between skin or undergarments and the zipper;

disposing a first thermoplastic material on a first end of an elongated steel boning that flexes in two or more directions;

disposing a second thermoplastic material on a second end of the elongated steel boning;

sewing a casing comprising the elongated steel boning;

sewing the casing into a back-support panel, the back-support panel comprising one or more elongated steel bonings;

sewing a first edge of the back-support panel, a first edge of a first lacing panel, and a first edge of a second right panel at a first seam at a back side of the orthopedic corset; and sewing a second edge of the back-support panel, a first edge of a second lacing panel, and a first edge of a second left panel at a second seam at the back side of the orthopedic corset, wherein the first lacing panel comprises a first set of reinforcement rings, and the second lacing panel comprises a second set of reinforcement rings, and wherein a first lace and a second lace are laced through alternating ones of the first set and the second set of reinforcement rings to adjust a tightness of the orthopedic corset;

sewing a second edge of the second right panel to a third right panel at the back side of the orthopedic corset, the third right panel comprising an additional elongated boning;

sewing the third right panel to a fourth right panel at the back side of the orthopedic corset;

sewing a second edge of the second left panel to a third left panel at the back side of the orthopedic corset, the third left panel comprising an additional elongated boning;

sewing the third left panel to a fourth left panel at the back side of the orthopedic corset;

sewing a right-side section between the fourth right panel and the first right panel; and sewing a left-side section between the fourth left panel and the first left panel.

19. The method of claim 18, further comprising bonding interfacing fabric to an interior of the casing, wherein:

the back-support panel comprises a first outer fabric; and the first lacing panel and the second lacing panel each comprises a second outer fabric, wherein the first outer fabric is more flexible than the second outer fabric.

20. The method of claim 18, further comprising:

sewing an additional elongated boning into the first right panel; and sewing an additional elongated boning into the first left panel.

\* \* \* \* \*